(12) United States Patent
Jeon

(10) Patent No.: US 9,372,134 B2
(45) Date of Patent: Jun. 21, 2016

(54) MICROFLUIDIC DEVICE AND METHOD FOR ISOLATING TARGET USING SAME

(75) Inventor: Byung Hee Jeon, Seongnam-si (KR)

(73) Assignee: CYTOGEN CO., LTD., Seongnam-si, Gyeonggi-do (KR)

( * ) Notice: Subject to any disclaimer, the term of this patent is extended or adjusted under 35 U.S.C. 154(b) by 686 days.

(21) Appl. No.: 13/641,094

(22) PCT Filed: Apr. 15, 2011

(86) PCT No.: PCT/KR2011/002705
§ 371 (c)(1),
(2), (4) Date: Dec. 11, 2012

(87) PCT Pub. No.: WO2011/129651
PCT Pub. Date: Oct. 20, 2011

(65) Prior Publication Data
US 2013/0074613 A1    Mar. 28, 2013

(30) Foreign Application Priority Data

Apr. 15, 2010  (KR) .................. 10-2010-0035005
Apr. 15, 2010  (KR) .................. 10-2010-0035012
Apr. 15, 2010  (KR) .................. 10-2010-0035013

(51) Int. Cl.
*G01N 1/34*       (2006.01)
*G01N 33/49*      (2006.01)
(Continued)

(52) U.S. Cl.
CPC ............ *G01N 1/34* (2013.01); *B01L 3/502753* (2013.01); *G01N 1/4077* (2013.01);
(Continued)

(58) Field of Classification Search
CPC ............... B01L 3/502746; B01L 3/502753; B01L 2300/0816; B01L 2300/0819; B01L 2400/086; G01N 1/34; G01N 1/4077; G01N 1/4088; G01N 15/02; G01N 15/0272; G01N 33/491; G01N 35/1095; G01N 2015/0288; G01N 2035/00158; G01N 2035/053
USPC .......... 73/863.21–863.24; 422/502–505, 507, 422/513, 522–523, 947, 956; 436/177
See application file for complete search history.

(56) References Cited

U.S. PATENT DOCUMENTS 5,624,815 A * 4/1997 Grant et al. ............ 73/863.23 X
5,800,784 A * 9/1998 Horn ............................ 422/535
(Continued)

FOREIGN PATENT DOCUMENTS

CN         1628907 A        6/2005
CN         101947516 A *    1/2011  ............ B07B 13/04
(Continued)

OTHER PUBLICATIONS

Derwent abstract of JP 2009-109232 A, ACC-No. 2009-J61096, and JPO machine translation of JP 2009-1092232 A (JP 2009-109232 A published May 21, 2009).*
(Continued)

*Primary Examiner* — Paul West
(74) *Attorney, Agent, or Firm* — Knobbe Martens Olson & Bear LLP

(57) ABSTRACT

A micro-fluidic device includes a filter case, a first capture array and a second capture array. The filter case includes an inlet for introducing a sample containing different kinds of targets, an outlet for discharging the sample and a channel extending between the inlet and the outlet. The first capture array is arranged in an upstream portion of the channel, the first capture array including a plurality of first forward funnels arranged along a direction orthogonal to a flow direction of the sample so as to capture the different kinds of targets. The second capture array is arranged in a downstream portion of the channel, the second capture array including a plurality of second forward funnels arranged along the direction orthogonal to the flow direction of the sample so as to capture the different kinds of targets.

19 Claims, 27 Drawing Sheets

(51) Int. Cl.
*G01N 1/40* (2006.01)
*B01L 3/00* (2006.01)
*G01N 15/02* (2006.01)
*G01N 35/10* (2006.01)
*G01N 35/00* (2006.01)

(52) U.S. Cl.
CPC ......... *G01N33/491* (2013.01); *B01L 3/502746* (2013.01); *B01L 2300/0816* (2013.01); *B01L 2400/086* (2013.01); *G01N 15/02* (2013.01); *G01N 35/1095* (2013.01); *G01N 2035/00158* (2013.01); *G01N 2035/1053* (2013.01)

(56) References Cited

U.S. PATENT DOCUMENTS

| | | | |
|---|---|---|---|
| 7,064,321 | B2* | 6/2006 | Franzen ................ 250/289 |
| 2004/0141880 | A1 | 7/2004 | Handler et al. |
| 2007/0259424 | A1 | 11/2007 | Toner et al. |
| 2009/0100810 | A1* | 4/2009 | Smith ..................... 55/343 |
| 2009/0226957 | A1* | 9/2009 | Paterlini-Brechot . G01N 1/4077 |
| 2009/0314725 | A1* | 12/2009 | Parro .................... 210/800 |
| 2011/0008223 | A1* | 1/2011 | Tsao et al. .............. 422/502 |
| 2011/0083964 | A1* | 4/2011 | Ulmanella ............... 204/643 |
| 2013/0244906 | A1* | 9/2013 | Collins ........... B01L 2300/0816 |
| 2015/0118739 | A1* | 4/2015 | Kobayashi .............. 422/502 X |

FOREIGN PATENT DOCUMENTS

| | | | | |
|---|---|---|---|---|
| CN | 101963552 A | * | 2/2011 | ............ G01N 1/20 |
| EP | 12740 A1 | * | 6/1980 | ............ G01N 15/02 |
| JP | 2003-102710 A | | 4/2003 | |
| JP | 2005-140790 A | | 6/2005 | |
| JP | 2008-526251 A | | 7/2008 | |
| JP | 2009-109232 A | | 5/2009 | |

OTHER PUBLICATIONS

English Translation of International Preliminary Report on Patentability for PCT/KR2011/002705, report issued Oct. 16, 2012.*
International Search Report dated Feb. 6, 2012 of PCT/KR2011/002705 which is the parent application—2 pages.
Suk Ho Kang, Particle Technology, SciTech 1995, p. 34 , in Korean.
Notification of Reasons for Rejection dated Nov. 26, 2014 of corresponding Japanese Patent Application No. 2013-504835—4 pages.
Notification of Reasons for Rejection dated Dec. 20, 2013 of corresponding Chinese Patent Application No. 201180029403.3—8 pages.

* cited by examiner

MICROFLUIDIC DEVICE AND METHOD FOR ISOLATING TARGET USING SAME

FIELD OF THE INVENTION

The present invention relates to a micro-fluidic device and, more particularly, to a micro-fluidic device for separating targets from a sample and a target separating method using the same.

BACKGROUND OF THE INVENTION

In recent years, regulations are tightened on a biological test and a clinical test conducted for the sake of treatment of human diseases. As an alternative for the biological test and the clinical test, research and development have been extensively made on the collection of live cells from the human blood. The collection of cells is conducted by different kinds of cell collecting devices such as a micro-fluidic device, a CTC (Circulating Tumor Cell) chip, a filter, and so forth.

U.S. Patent Publication No. 2007/0259424A1 discloses a micro-fluidic device. The micro-fluidic device disclosed in this patent document includes a top layer, a bottom layer and a plurality of obstacles. Binding moieties, e.g., antibodies, charged polymers, or molecules coupled with cells are coated on the surfaces of the obstacles. The obstacles include microposts extending in a height direction from the surface of the top layer or the bottom layer. A sample, e.g., the blood, is admitted through an inlet of the top layer to flow along channels and is then discharged through an outlet of the top layer. The cells contained in the blood are captured by the binding moieties.

SUMMARY OF THE INVENTION

Technical Problems

However, the micro-fluidic device stated above suffers from a problem in that the capture rate of targets is very low. This is because the targets are captured by merely bonding the targets to the binding moieties. Moreover, the micro-fluidic device has a difficulty in collecting the targets captured by the binding moieties. The micro-fluidic device is not suitable for use in separating the targets from a large quantity of blood and in testing and analyzing the targets thus separated.

In view of the problems noted above, it is an object of the present invention to provide a micro-fluidic device capable of efficiently separating targets contained in a sample and a target separating method using the same.

Another object of the present invention is to provide a micro-fluidic device capable of capturing targets from a sample containing targets and non-targets through the use of funnels, overturning the funnels to face in the direction opposite to the capturing direction of the targets and consequently separating and collecting the targets with ease, and a target separating method using the same.

Means for Solving the Problems

In accordance with one aspect of the present invention, there is provided a micro-fluidic device, comprising: a filter case including an inlet for introducing a sample containing different kinds of targets, an outlet for discharging the sample and a channel extending between the inlet and the outlet; a first capture array arranged in an upstream portion of the channel, the first capture array including a plurality of first forward funnels arranged along a direction orthogonal to a flow direction of the sample so as to capture the different kinds of targets; and a second capture array arranged in a downstream portion of the channel, the second capture array including a plurality of second forward funnels arranged along the direction orthogonal to the flow direction of the sample so as to capture the different kinds of targets.

In accordance with another aspect of the present invention, there is provided a target separating method, comprising the steps of: providing a micro-fluidic device including a filter case having a channel through which a sample containing different kinds of targets can flow and a plurality of capture arrays arranged in multiple stages along a flow direction of the sample, each of the capture arrays including a plurality of forward funnels arranged within the channel along a direction orthogonal to the flow direction of the sample so as to capture the different kinds of targets and a reverse flow guide means for causing the different kinds of targets captured in the forward funnels to flow in a direction opposite to the flow direction of the sample when the filter case is mounted in an overturned state; supplying the sample into the channel to capture the different kinds of targets with the forward funnels; turning the filter case upside down such that the forward funnels are arranged in an overturned state; supplying a carrier fluid into the channel to discharge the different kinds of targets captured by the forward funnels out of the filter case; and collecting the different kinds of targets discharged out of the filter case.

Effect of the Invention

The micro-fluidic device and the target separating method according to the present invention can efficiently capture and separate targets from a sample. In addition, the micro-fluidic device and the target separating method are capable of capturing targets from a sample containing targets and non-targets through the use of funnels, overturning the funnels to face in the direction opposite to the capturing direction of the targets and consequently separating and collecting the targets with ease. Accordingly, the micro-fluidic device and the target separating method are very useful in separating and collecting cells from the human blood and so forth.

DETAILED DESCRIPTION OF THE EMBODIMENTS

Figure 1:
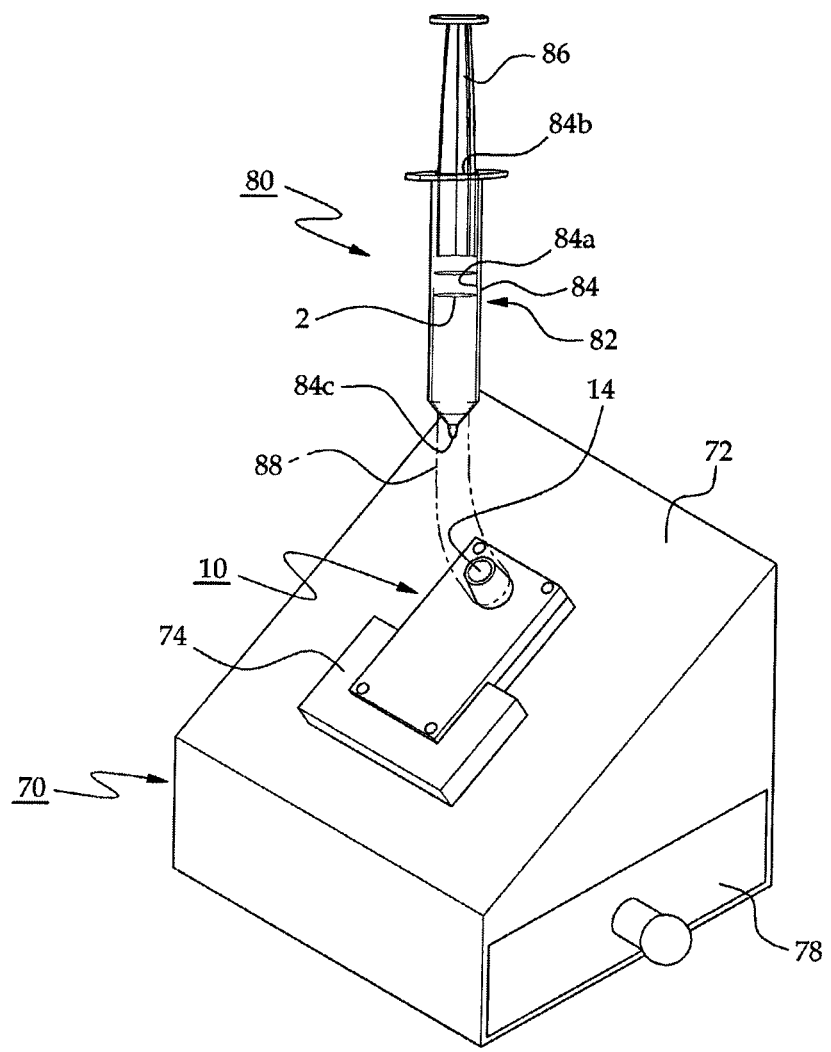
FIG. 1 is a perspective view showing the configuration of a micro-fluidic device according to a first embodiment of the present invention.

Other objects, specific advantages and novel features of the present invention will become apparent from the following description of preferred embodiments made in conjunction with the accompanying drawings.

Certain preferred embodiments of a micro-fluidic device according to the present invention will now be described in detail with reference to the accompanying drawings.

FIGS. 1 through 10 show a micro-fluidic device according to a first embodiment of the present invention. Referring to FIGS. 1 through 4, the micro-fluidic device according to the first embodiment of the present invention includes a filter case 10 forming an outer shell. The filter case 10 includes an upper case part 10*a* and a lower case part 10*b* removably coupled to the rear surface of the upper case part 10*a*. A channel 12 through which a sample 2 flows from an upstream end toward a downstream end is formed within the filter case 10. An inlet 14 for introducing the sample 2 is connected to the upstream end of the channel 12. An outlet 16 for discharging the sample 2 is connected to the downstream end of the channel 12. The inlet 14 is formed in a ,front upper portion of the upper case part 10*a*. The outlet 16 is formed in a rear lower portion of the lower case part 10*b*.

Figure 5:
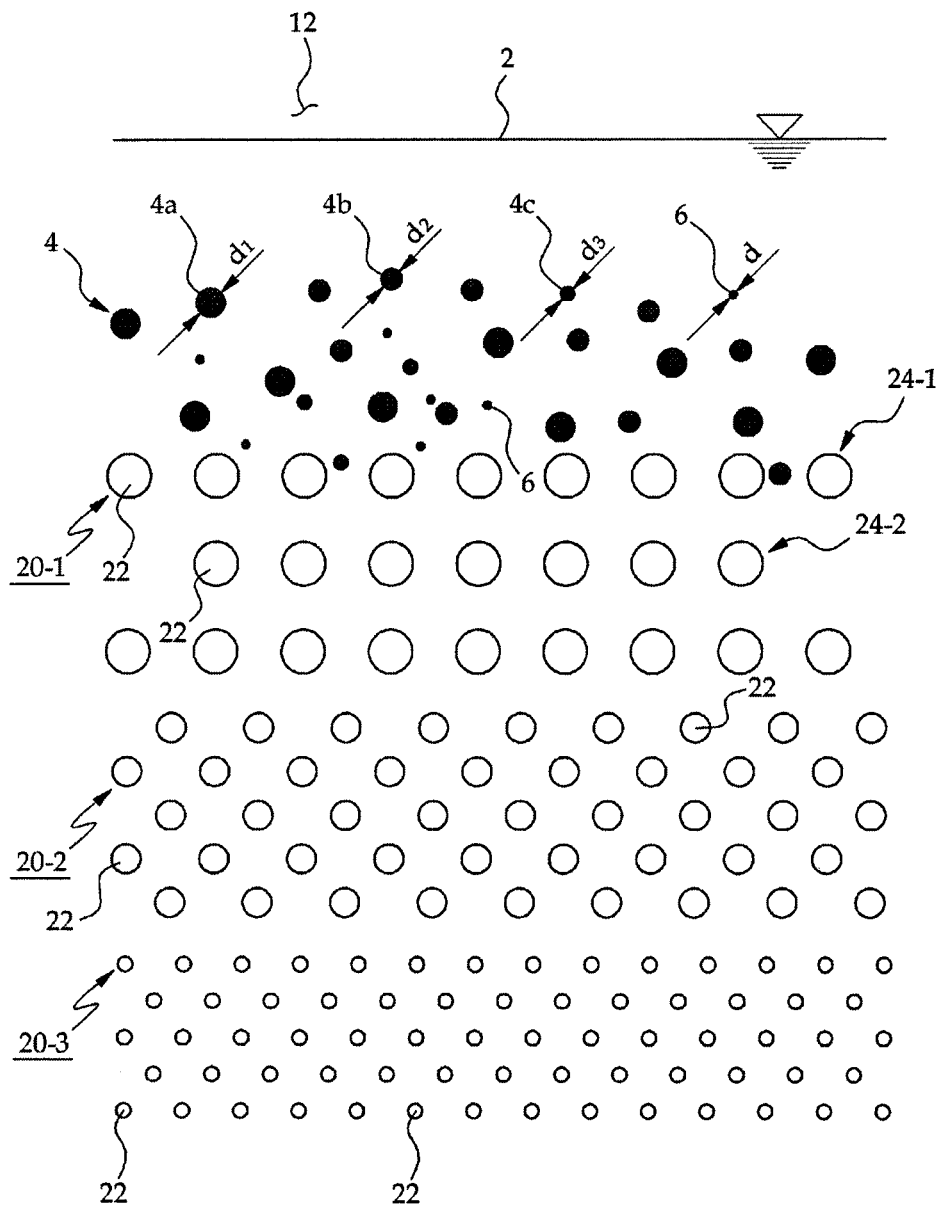
FIG. 5 is a front view showing the configuration of a dispersing unit employed in the micro-fluidic device according to the first embodiment of the present invention.
Figure 6:
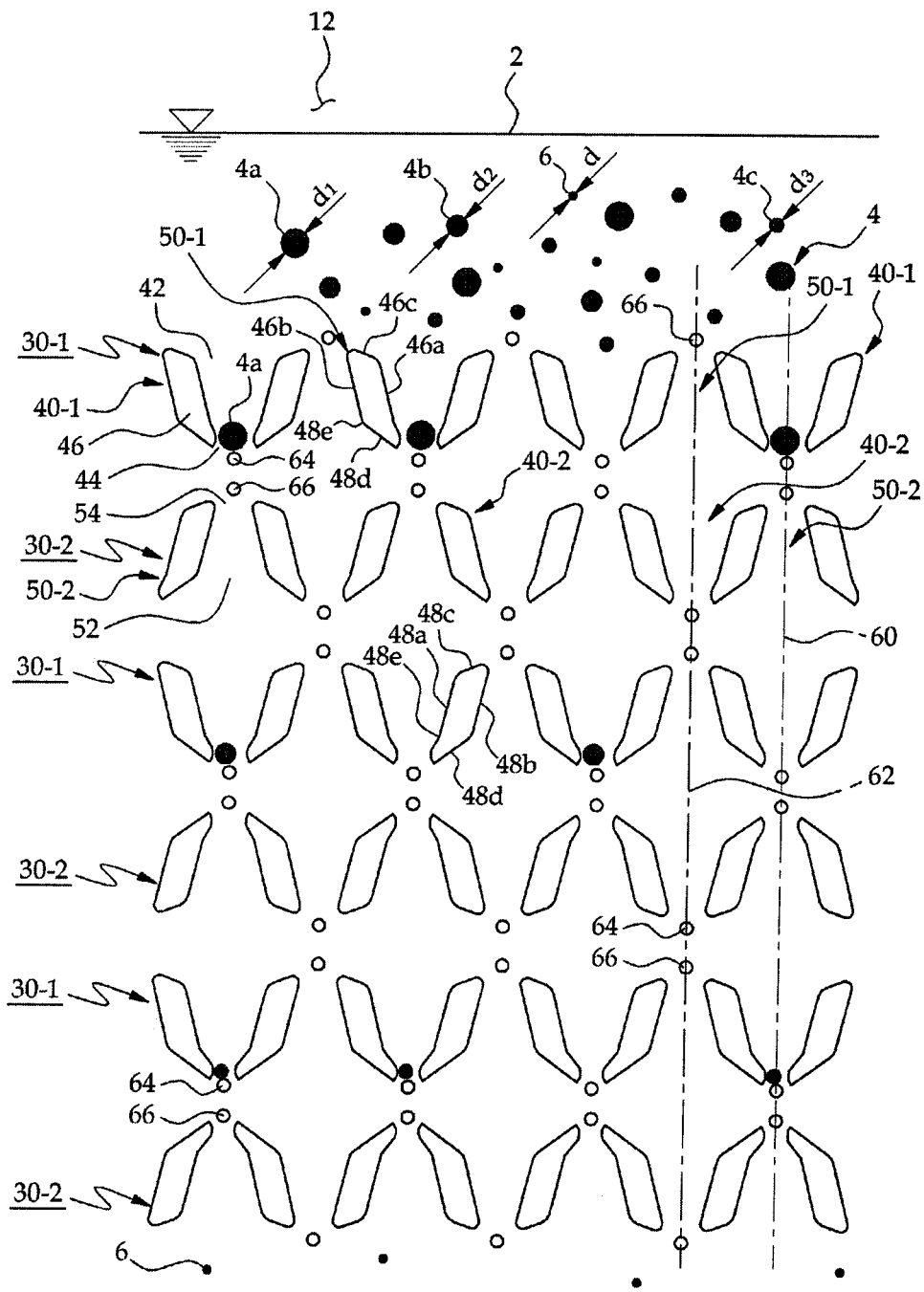
FIG. 6 is a front view showing the configuration of first and second capture arrays employed in the micro-fluidic device according to the first embodiment of the present invention.

As shown in FIGS. 5 and 6, the sample 2 contains different kinds of targets 4 (4*a*, 4*b* and 4*c*) differing in size from each other and a plurality of non-targets 6. The targets 4 include first kind targets 4*a*, second kind targets 4*b* and third kind targets 4*c*. The first kind targets 4*a* have a first diameter $d_1$. The second kind targets 4*b* have a second diameter $d_2$. The third kind targets 4*c* have a third diameter $d_3$. The first diameter $d_1$ is larger than the second diameter $d_2$. The second diameter $d_2$ is larger than the third diameter $d_3$. The non-targets 6 have a diameter d smaller than the third diameter $d_3$ of the third kind targets 4*c*.

The sample 2 may be the physiological fluid such as saliva, sweat or urine, the blood or the serum of a human or an animal. In addition, the fluid containing targets 6 such as cells or tissues of a human, an animal or a plant and the fluid containing viruses or bacteria may be selected as the sample 2. If the blood is selected as the sample 2, the cells of different sizes contained in the blood may become the targets 6. Examples of the cells contained in the blood include red blood cells and white blood cells.

Figure 2:
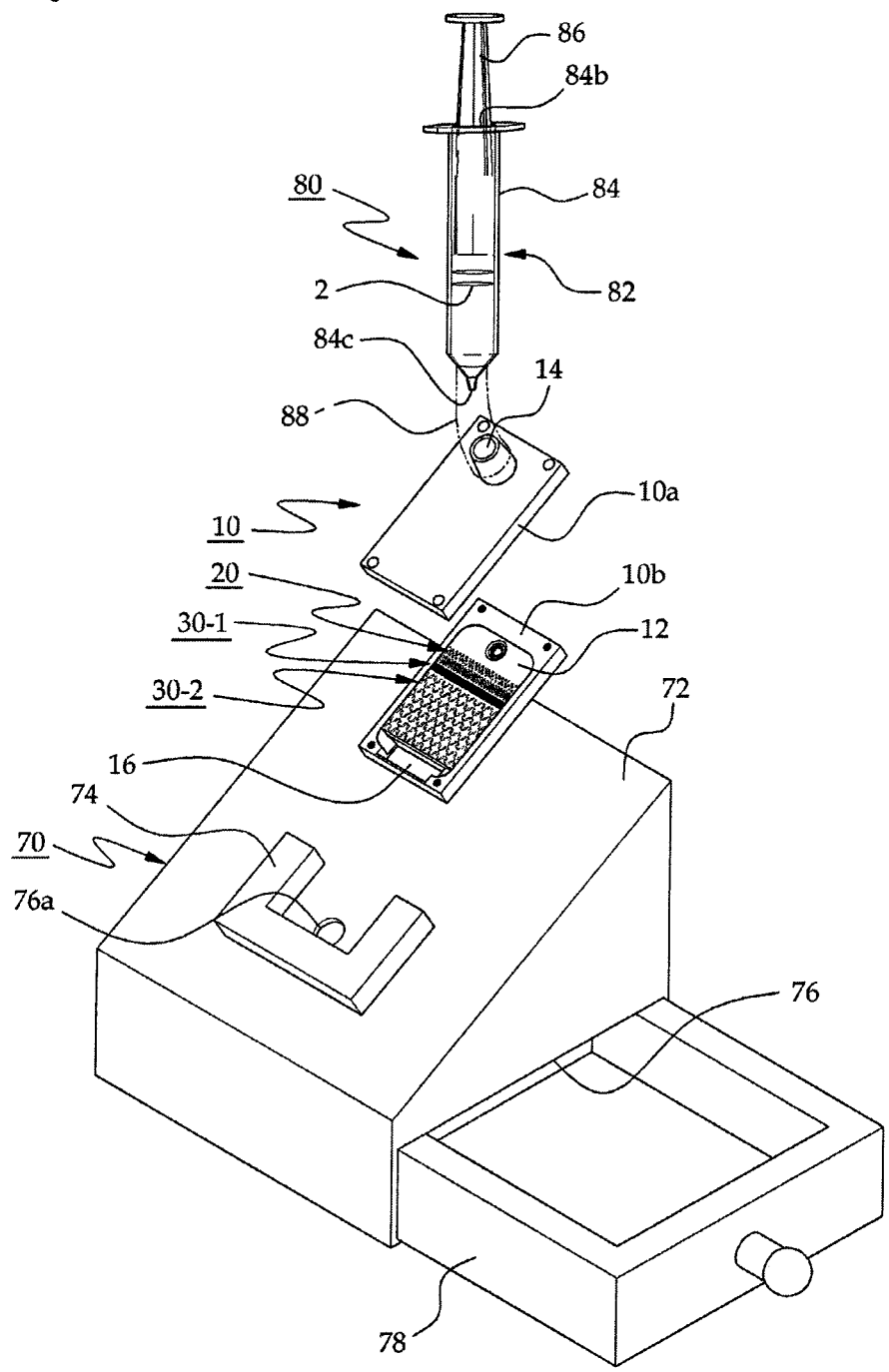
FIG. 2 is a perspective view of the micro-fluidic device according to the first embodiment of the present invention, showing a filter case in an exploded state.
Figure 4:
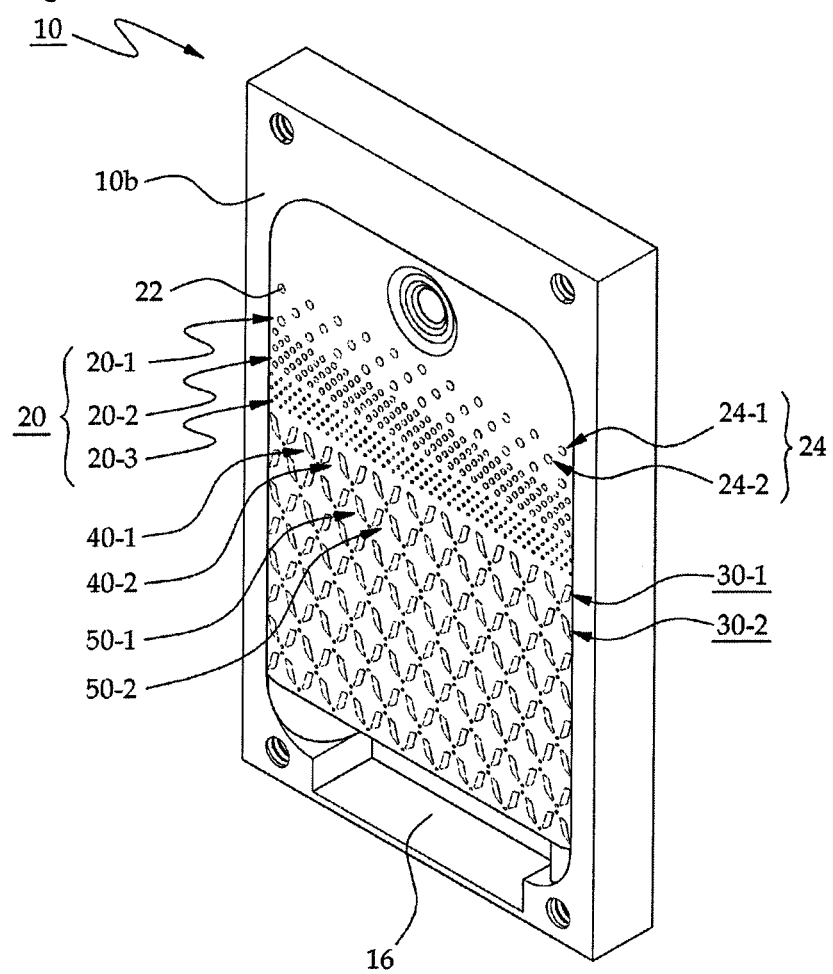
FIG. 4 is a perspective view showing a lower case part of a filter case employed in the micro-fluidic device according to the first embodiment of the present invention, with an upper case part removed for clarity.

Referring to FIGS. 2, 4 and 5, the micro-fluidic device according to the first embodiment of the present invention includes a plurality of dispersing units 20 (20-1, 20-2 and 20-3) arranged in the upstream portion of the channel 12 to disperse the sample 2 flowing along the flow direction of the sample 2. The dispersing units 20 includes a first dispersing unit 20-1, a second dispersing unit 20-2 and a third dispersing unit 20-3 arranged along the flow direction of the sample 2 in multiple stages.

Each of the first to third dispersing units 20-1, 20-2 and 20-3 includes post arrays 24 (24-1 and 24-2) each having a plurality of posts 22 arranged in a spaced-apart relationship along the flow direction of the sample 2 and along the direction orthogonal to the flow direction of the sample 2. The interval between the posts 22 is set to allow the targets 4 to pass through between the posts 22. In the post arrays 24 of each of the first to third dispersing units 20-1, 20-2 and 20-3, the posts 22 of the odd-number post arrays 24-1 and the posts 22 of the even-number post arrays 24-2 counted from the upstream end toward the downstream end of the channel 12 are arranged in a staggering pattern. With this arrangement of the posts 22, when the odd-number post arrays 24-1 are viewed from the inlet 14, the posts 22 of the even-number post arrays 24-2 are seen between the posts 22 of the odd-number post arrays 24-1.

The posts 22 of the first to third dispersing units 20-1, 20-2 and 20-3 are arranged such that the diameter thereof are gradually reduced along the flow direction of the sample 2. For example, the posts 22 of the first dispersing unit 20-1 may be formed to have a diameter of from 300 μm to 400 μm. The posts 22 of the second dispersing unit 20-2 may be formed to have a diameter of from 200 μm to 300 μm. The posts 22 of the third dispersing unit 20-3 may be formed to have a diameter of from 100 μm to 200 μm. In FIG. 5, the posts 22 are shown to have a circular cross section by way of example. However, the cross section of the posts 22 may have many other different shapes capable of efficiently dispersing the flow of the sample 2, e.g., an elliptical shape, a triangular shape, a rectangular shape or a pentagonal shape.

Referring to FIGS. 2, 4, 6 and 7, the micro-fluidic device according to the first embodiment of the present invention includes first capture arrays 30-1 and second capture arrays 30-2 which are arranged along the flow direction of the sample 2 at the downstream side of the dispersing units 20 so as to capture the targets 4. The first capture arrays 30-1 are arranged adjacent to the downstream end of the dispersing units 20. Each of the first capture arrays 30-1 includes a plurality of first forward funnels 40-1 and a plurality of first reverse funnels 50-1 alternately arranged along the direction orthogonal to the flow direction of the sample 2. The second capture arrays 30-2 are arranged adjacent to the downstream ends of the first capture arrays 30-1. Each of the second capture arrays 30-2 includes a plurality of second forward funnels 40-2 and a plurality of second reverse funnels 50-2 alternately arranged along the direction orthogonal to the flow direction of the sample 2. The first and second reverse funnels 50-1 and 50-2 make up a reverse flow inducing means that causes the different kinds of targets 4 captured in the first and second forward funnels 40-1 and 40-2 to flow in the direction opposite to the flow direction of the sample 2 when the filter case 10 is mounted in an overturned state.

Each of the first and second forward funnels 40-1 and 40-2 has an entrance 42 formed at the upstream side of the channel 12 along the flow direction of the sample 2 and an exit 44 formed at the downstream side of the channel 12. The cross-sectional area of each of the first and second forward funnels 40-1 and 40-2 is gradually decreased from the entrance 42 toward the exit 44. Each of the first and second reverse funnels 50-1 and 50-2 has an entrance 52 formed at the downstream side of the channel 12 along the flow direction of the sample 2 and an exit 54 formed at the upstream side of the channel 12. The cross-sectional area of each of the first and second reverse funnels 50-1 and 50-2 is gradually decreased from the entrance 52 toward the exit 54. The cross-sectional area of the exit 44 of each of the first forward funnels 40-1 is equal to the cross-sectional area of the exit 54 of each of the first reverse funnels 50-1. The cross-sectional area of the exit 44 of each of the second forward funnels 40-2 is equal to the cross-sectional area of the exit 54 of each of the second reverse funnels 50-2.

Each of the first and second forward funnels 40-1 and 40-2 includes a first guide 46 and a second guide 48 which are provided in pair. The first guide 46 includes a first slant surface 46a and a second slant surface 46b obliquely extending in a parallel relationship with each other. The second guide 48 includes a first slant surface 48a and a second slant surface 48b obliquely extending in a parallel relationship with each other. The first slant surface 46a of the first guide 46 and the first slant surface 48a of the second guide 48 face each other. The first guide 46 further includes a third slant surface 46c formed at the top end thereof to obliquely extend from the second slant surface 46b of the first guide 46 toward the entrance 42. The second guide 48 further includes a third slant surface 48c formed at the top end thereof to obliquely extend from the second slant surface 48b of the second guide 48 toward the entrance 42. The first guide 46 further includes a fourth slant surface 46d formed at the bottom end thereof to obliquely extend from the second slant surface 46b of the first guide 46 toward the exit 44. The second guide 48 further includes a fourth slant surface 48d formed at the bottom end thereof to obliquely extend from the second slant surface 48b of the second guide 48 toward the exit 44. The first guide 46 further includes round corners 46e where the first through fourth slant surfaces 46a, 46b, 46c and 46d meet with one another. The second guide 48 further includes round corners 48e where the first through fourth slant surfaces 48a, 48b, 48c and 48d meet with one another. The round corners 46e and 48e serve to assure smooth flow of the targets 4 and to prevent the targets 4 from getting damaged.

Each of the first and second reverse funnels 50-1 and 50-2 is arranged between the first and second forward funnels 40-1 and 40-2 adjoining to each other. Each of the first and second reverse funnels 50-1 and 50-2 is formed of the first guide 46 of each of the first and second forward funnels 40-1 and 40-2 arranged at the right side thereof and the second guide 48 of each of the first and second forward funnels 40-1 and 40-2 arranged at the left side thereof. The first forward funnels 40-1 and the second forward funnels 40-2 are arranged in a staggering pattern with respect to each other. The first reverse funnels 50-1 and the second reverse funnels 50-2 are arranged in a staggering pattern with respect to each other. In other words, the second forward funnels 40-2 are arranged below the first reverse funnels 50-1. The second reverse funnels 50-2 are arranged below the first forward funnels 40-1. The first forward funnels 40-1 and the second reverse funnels 50-2 are arranged on a first axis 60 parallel to the flow direction of the sample 2. The first reverse funnels 50-1 and the second forward funnels 40-2 are arranged on a second axis 62 parallel to the flow direction of the sample 2.

The first and second capture arrays 30-1 and 30-2 are arranged in multiple stages along the flow direction of the sample 2. The first and second capture arrays 30-1 and 30-2 are alternately arranged along the flow direction of the sample 2. In FIGS. 4 and 6, the first and second capture arrays 30-1 and 30-2 are arranged in eight rows, namely four rows for each array, by way of example. If necessary, the number of each of the first and second capture arrays 30-1 and 30-2 may be appropriately changed. The first and second capture arrays 30-1 and 30-2 are arranged such that the cross-sectional area of the exit 44 of each of the first and second forward funnels 40-1 and 40-2 is gradually reduced toward the downstream side along the flow direction of the sample 2. The first and second capture arrays 30-1 and 30-2 are arranged such that the cross-sectional area of the exit 44 of each of the first and second reverse funnels 50-1 and 50-2 is gradually increased toward the upstream along the direction opposite to the flow direction of the sample 2.

Figure 7:
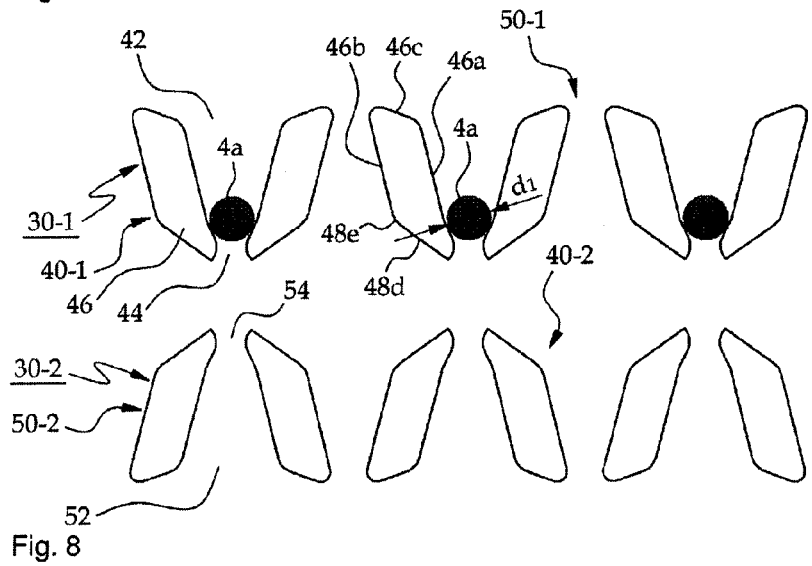
FIG. 7 is a section view showing a modified example of the first and second capture arrays employed in the micro-fluidic device according to the first embodiment of the present invention.

First obstruction bodies 64 are arranged near the downstream ends of the exits 44 of the first and second forward funnels 40-1 and 40-2. The first obstruction bodies 64 obstruct the targets 4 flowing out of the exits 44 and assist the first and second forward funnels 40-1 and 40-2 in capturing the targets 4. Second obstruction bodies 66 are arranged near the upstream ends of the first and second reverse funnels 50-1 and 50-2 so that the targets 4 can flow in the direction opposite to the capturing direction in which the targets 4 are captured by the first and second forward funnels 40-1 and 40-2 and can flow out of the exits 54. The second obstruction bodies 66 serve as guides for guiding the flow of the targets 4 toward the first and second forward funnels 40-1 and 40-2. As shown in FIG. 7, the first obstruction bodies 64 and the second obstruction bodies 66 may be omitted. In that case, the targets 4 are captured within the first and second forward funnels 40-1 and 40-2.

Figure 3:
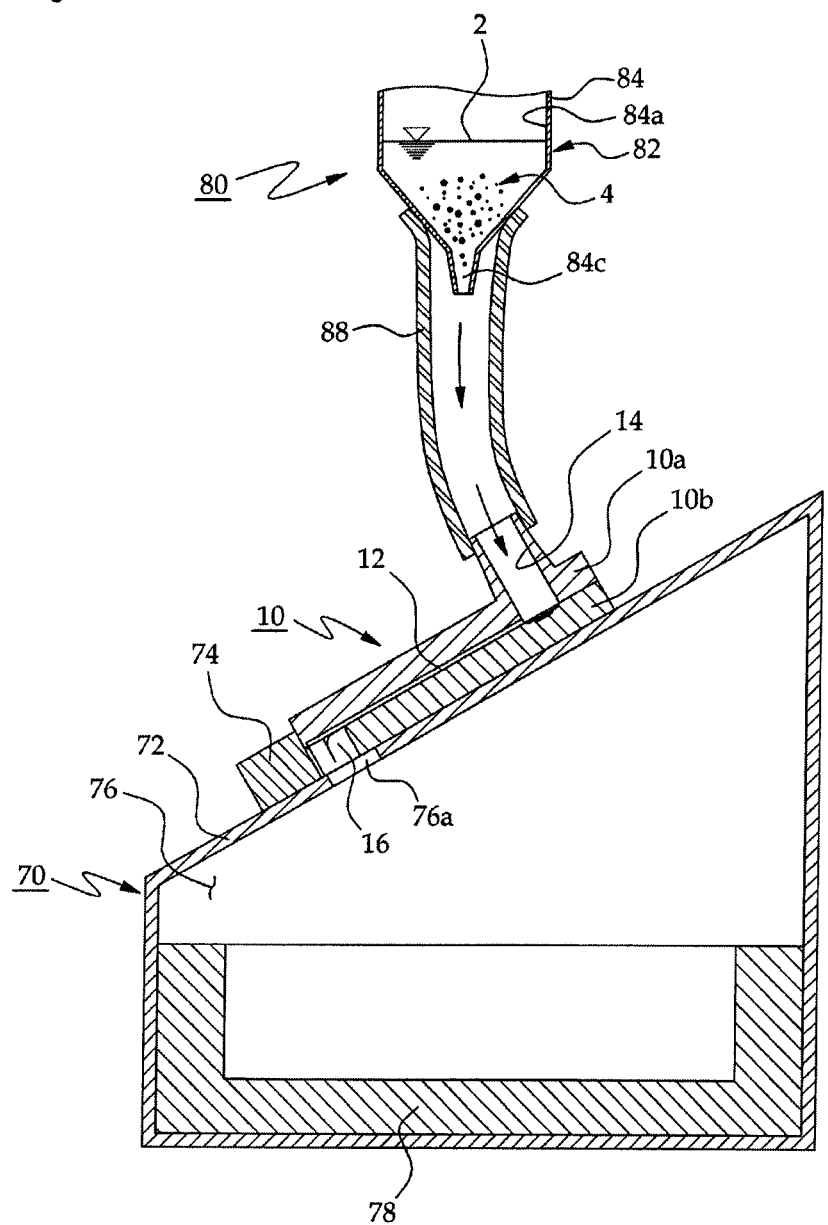
FIG. 3 is a section view showing the configuration of the micro-fluidic device according to the first embodiment of the present invention.

Referring to FIGS. 1 through 3, the micro-fluidic device according to the first embodiment of the present invention includes a stand 70 on which the filter case 10 can be obliquely placed. The stand 70 includes a slant table 72 on which the filter case 10 can be obliquely placed and a holder 74 to which the edge of the filter case 10 can be fitted. A space 76 for receiving the sample 2 is formed within the stand 70. An introduction hole 76a for introducing the sample 2 discharged through the outlet 16 of the filter case 10 into the space 76 is formed on the upper surface of the slant table 72. A container 78 for receiving the sample 2 introduced into the space 76 of the stand 70 is positioned below the slant table 72. The introduction hole 76a is arranged above the container 78. The container 78 can be slid into and out of the space 76 like a drawer.

The micro-fluidic device according to the first embodiment of the present invention includes syringe 82 as a sample supply unit 80 for storing the sample 2 and supplying the sample 2 into the inlet 14 of the filter case 10. The syringe 82 includes a cylinder 84 having a bore 84a for storing the sample 2, an inlet 84b for introducing the sample 2 and an outlet 84c for discharging the sample 2. The syringe 82 further includes a piston 86 inserted into the bore 84a through the inlet 84b. The piston 86 reciprocates along the bore 84a to discharge the sample 2 through the outlet 84c. The outlet 84c is connected to the inlet 14 of the filter case 10 through a hose 88. The sample supply unit 80 may be formed of a syringe pump or a plunger pump for pumping a specified amount of sample 2 and supplying the sample 2 into the channel 12 of the filter case 10. If the human blood is selected as one example of the sample 2, the sample supply unit 80 may be formed of a blood collection tube, a bag or a pack.

Description will now be described on the micro-fluidic device according to the first embodiment of the present invention.

Referring to FIGS. 1 through 4, the filter case 10 is obliquely placed on the upper surface of the slant table 72 when the filter case 10 is fitted to the holder 74. The inlet 14 of the filter case 10 is exposed at the upper side of the slant table 72. The outlet 16 of the filter case 10 is connected to the introduction hole 76a of the stand 70. The outlet 84c of the cylinder 84 is connected to the inlet 14 of the filter case 10 through the hose 88. If the piston 86 moves forward along the bore 84a of the cylinder 84, the sample 2 is discharged through the outlet 84c of the cylinder 84 and is introduced into the upstream portion of the channel 12 through the hose 88 and the inlet 14 of the filter case 10.

As shown in FIG. 5, the sample 2 is dispersed in the direction orthogonal to the flow direction of the sample 2 while passing through between the posts 22 of the first to third dispersing units 20-1, 20-2 and 20-3. Along with the flow of the sample 2, the targets 4 and the non-targets 6 contained in the sample 2 are uniformly dispersed in the transverse direction of the channel 12. The human blood as one example of the sample 2 may flow through the channel 12 in a biased state depending on the viscosity thereof. The flow of the blood is dispersed while sequentially passing through the first to third dispersing units 20-1, 20-2 and 20-3. This helps increase the capture rate of the targets 6 captured by the first and second capture arrays 30-1 and 30-2.

As shown in FIG. 6, the sample 2 flows down from the entrances 42 of the first forward funnels 40-1 toward to exits 44 thereof. If the exits 44 of the first forward funnels 40-1 have a width of from 15 μm to 20 μm, the first kind targets 4a having a size of 15 μm or more cannot pass through the exits 44. The second kind targets 4b, the third kind targets 4c and the non-targets 6, all of which have a size of less than 15 μm, can pass through the exits 44. The first obstruction bodies 64 obstruct the first kind targets 4a flowing out of the exits 44 of the first forward funnels 40-1. Thus the first kind targets 4a are captured by the first forward funnels 40-1.

Subsequently, the sample 2 passed through the first forward funnels 40-1 flows down from the entrances 42 of the second forward funnels 40-2 toward the exits 44 thereof. If the exits 44 of the second forward funnels 40-2 have a width of from 10 μm to 15 μm, the second kind targets 4b having a size of 10 μm or more cannot pass through the exits 44. The third kind targets 4c and the non-targets 6, both of which have a size of less than 10 μm, can pass through the exits 44. The second obstruction bodies 66 arranged between the first capture arrays 30-1 and the second capture arrays 30-2 guide the flow of the targets 4 toward the second forward funnels 40-2.

The third kind targets 4c are captured by the first and second capture arrays 30-1 and 30-2 arranged at the downstream side of the second capture arrays 30-2 in multiple stages. The non-targets 6 can pass through the first and second capture arrays 30-1 and 30-2. The exits 44 may be formed to have a minimum width of 5 μm. Normal cells such as red blood cells of the human blood, as one example of the non-targets 6, can easily pass through a hole having a diameter smaller than the diameter thereof because the cytoplasm surrounding the cell nucleus is deformable. As one example of the targets 4, cells low in the deformation ratio of a cytoplasm can hardly pass through a hole having a diameter smaller than the diameter thereof. The cytoplasm of each of the normal cell is deformed when making contact with the first obstruction bodies 64 and can easily pass through between the exits 44 and the first obstruction bodies 64. The non-targets 6 are introduced into the space through the outlet 16 of the filter case 10 and the introduction hole 76a of the stand 70 and are received within the container 78.

In this manner, the targets 4 are filtered and separated on a size-by-size basis by the first and second capture arrays 30-1 and 30-2 arranged in multiple stages. It is therefore possible to efficiently collect, e.g., white blood cells having a diameter of from 12 μm to 25 μm from the human blood. In case where the exits 44 are formed to have a width of 5 μm, red blood cells having a diameter of from 6 μm to 8 μm can pass through the exits 44 because the cytoplasm thereof is deformable.

Figure 8:
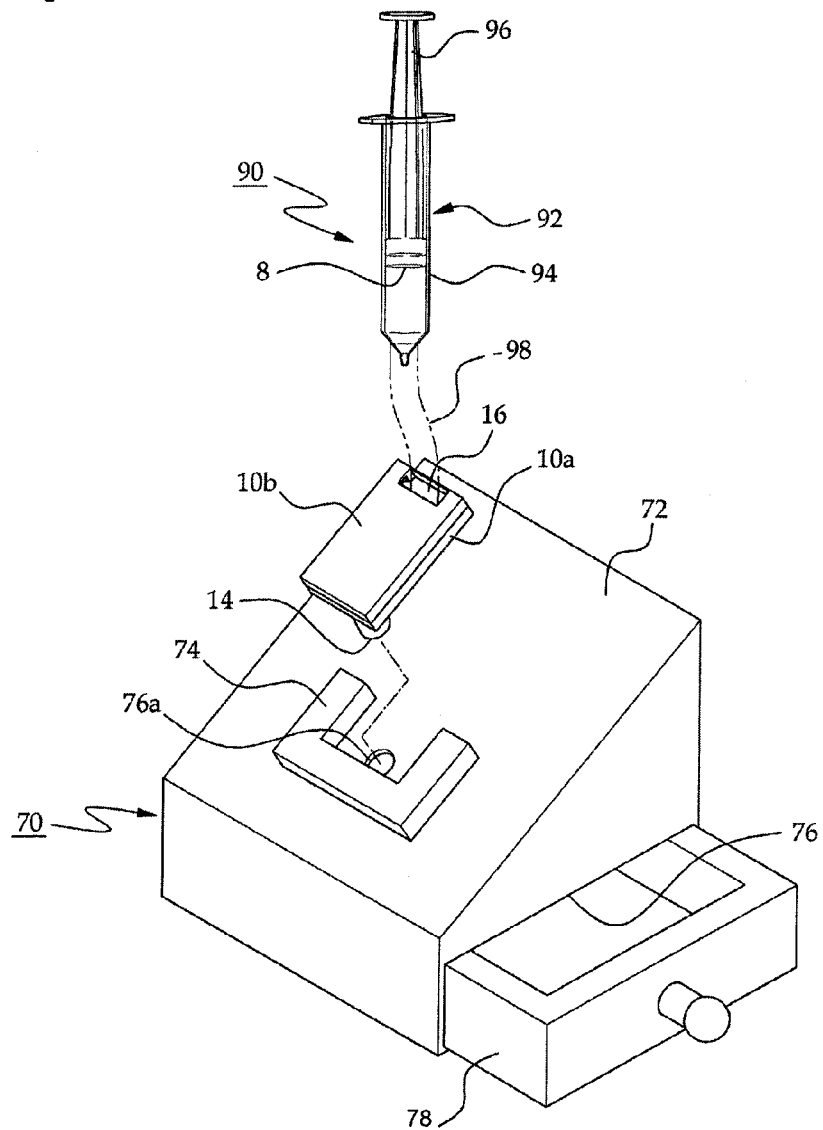
FIG. 8 is a perspective view for explaining how to install a filter case on a stand in an overturned state in the micro-fluidic device according to the first embodiment of the present invention.
Figure 9:
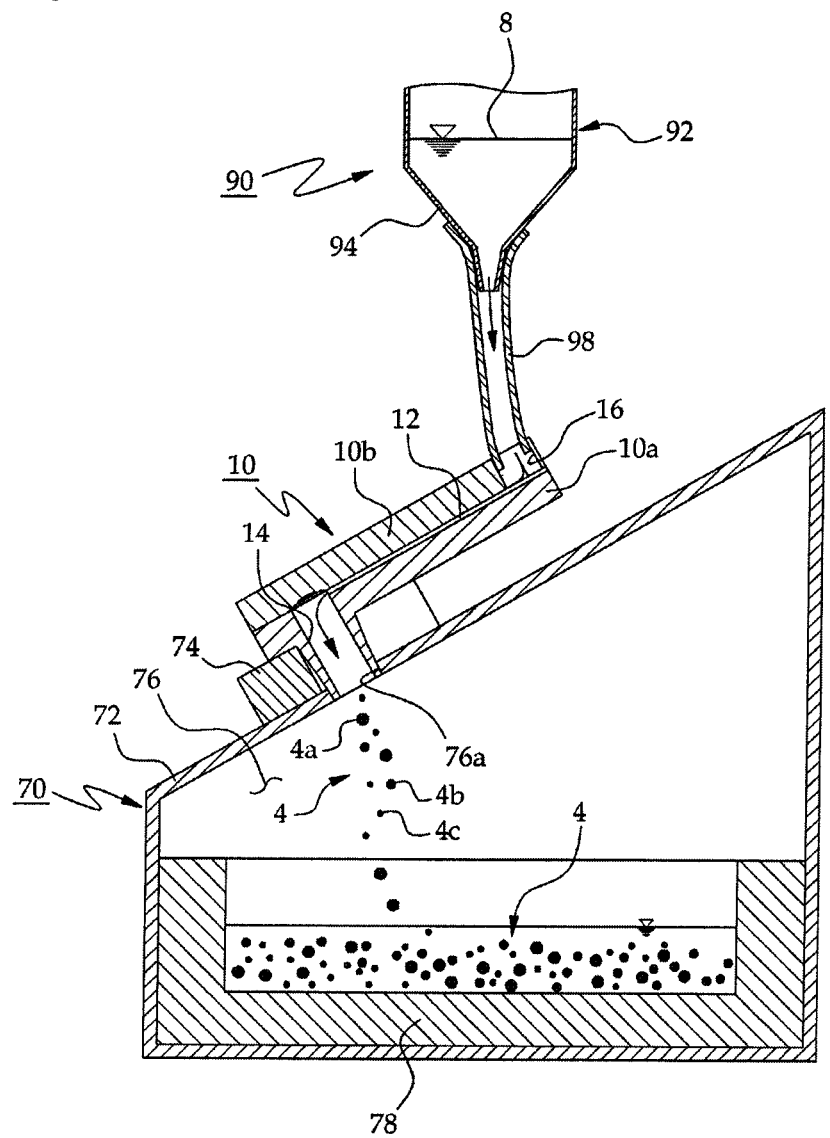
FIG. 9 is a section view showing the filter case installed on the stand in an overturned state in the micro-fluidic device according to the first embodiment of the present invention.
Figure 10:
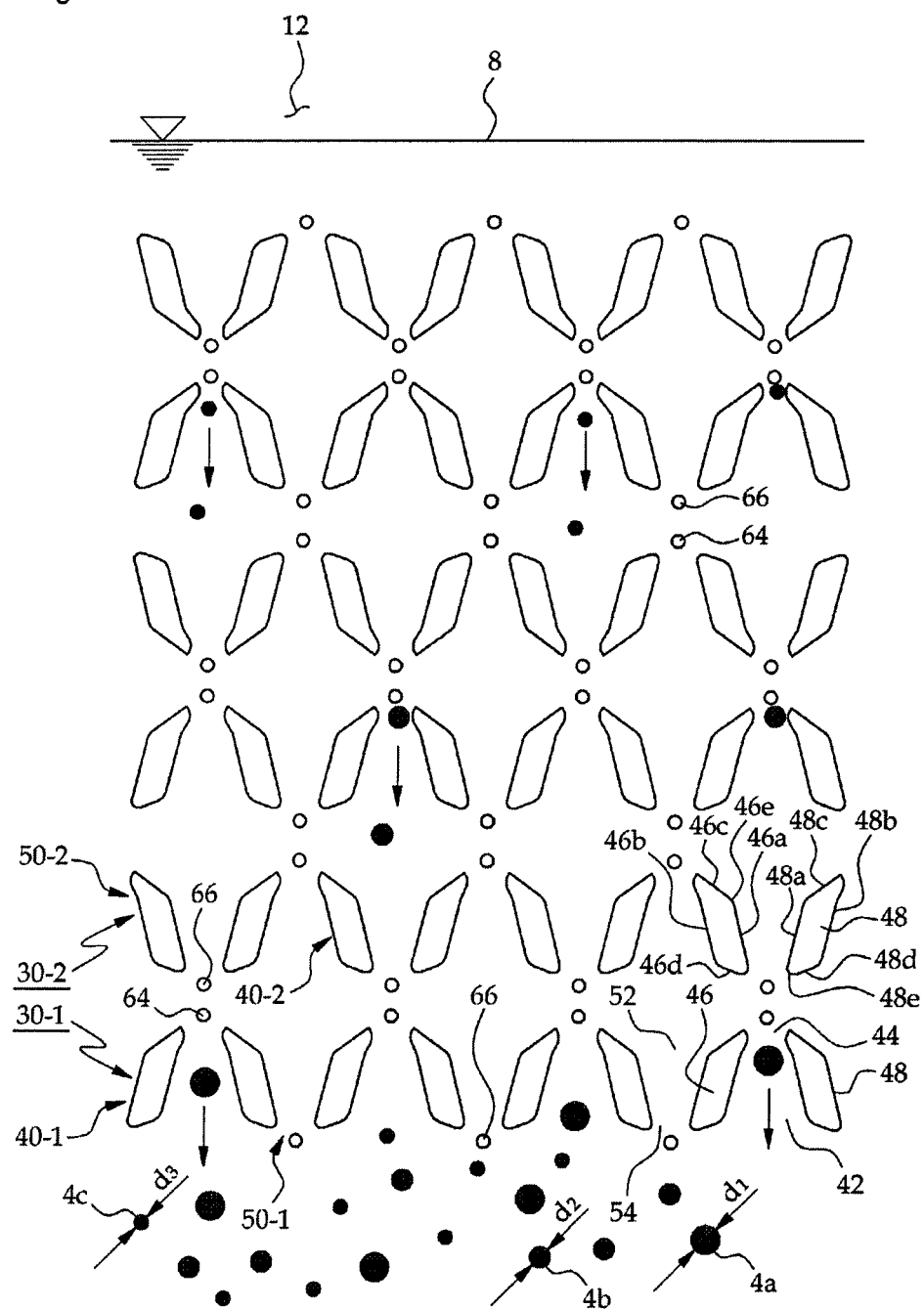
FIG. 10 is a front view for explaining how to separate targets from the first and second capture arrays in the micro-fluidic device according to the first embodiment of the present invention.

Referring to FIGS. 8 through 10, the micro-fluidic device according to the first embodiment of the present invention includes a carrier fluid supply unit 90 for supplying a carrier fluid, e.g., a solution 8, in order to separate and collect the targets 4 captured by the first and second capture arrays 30-1 and 30-2. The carrier fluid supply unit 90 is formed of a syringe 92. The syringe 92 includes a cylinder 94, a piston 96 and a hose 98. The configuration and operation of the syringe 92 are the same as those of the syringe 82 of the sample supply unit 80 and therefore will not be described in detail. The carrier fluid supply unit 90 may be formed of a syringe pump or a plunger pump for pumping and supplying a specified amount of solution 8.

The targets 4 captured by the first and second capture arrays 30-1 and 30-2 are separated and collected by a target separating method using the micro-fluidic device according to the first embodiment of the present invention. In order to collect the targets 4, the filter case 10 is fitted to the holder 74 by turning the filter case 10 upside down so that the inlet 14 can face downward with the outlet 16 facing upward. The inlet 14 of the filter case 10 is connected to the introduction hole 76a of the stand 70. If the filter case 10 is attached to the slant table 72 in an overturned state, the first and second forward funnels 40-1 and 40-2 are oriented in the direction opposite to the filtering direction so that the entrances 42 can be arranged at the downstream side of the channel 12 with the exits 44 arranged at the upstream side of the channel 12. The first and second reverse funnels 50-1 and 50-2 are oriented so that the entrances 52 can be arranged at the upstream side of the channel 12 with the exits 54 arranged at the downstream side of the channel 12.

If the piston 96 moves forward within the cylinder 94 after the outlet 16 of the filter case 10 is connected to the cylinder 94 by the hose 98, the solution 8 is discharged from the cylinder 94 and is introduced into the channel 12 through the hose 98 and the outlet 16 of the filter case 10. The solution 8 flows down from the entrances 52 of the second reverse funnels 50-2 toward the exits 54 thereof. Concurrently, the solution 8 flows down from the exits 44 of the second forward funnels 40-2 toward the entrances 42. As a result, the targets 4 captured by the second forward funnels 40-2, e.g., the second kind targets 4b, flow out of the entrances 42 of the second forward funnels 40-2 and flow toward the first capture arrays 30-1 along the channel 12.

Then, the targets 4 are introduced into the first reverse funnels 50-1 through the entrances 52 of the first reverse funnels 50-1. Thereafter, the targets 4 flow down toward the exits 54. The targets 4 flowing in the direction opposite to the capturing direction can easily pass through between the exits 54 and the second obstruction bodies 66. The second kind targets 4b passed through the exits 54 of the first reverse funnels 50-1 and the first kind targets 4a captured by the first forward funnels 40-1 flow, together with the solution 8, through the third dispersing unit 20-3, the second dispersing unit 20-2, the first dispersing unit 20-1, the inlet 14 of the filter case 10 and the introduction hole 76a of the stand 70 in the named order. Then, the second kind targets 4b and the first kind targets 4a are introduced into the space 76. The targets 4 and the solution 8 introduced into the space 76 are received in the container 78. The container 78 is then opened and the targets 4 received in the container 78 are collected.

FIGS. 11 through 17 show a micro-fluidic device according to a second embodiment of the present invention. The same components as those of the micro-fluidic device according to the first embodiment will be designated by like reference numerals and will not be described in detail.

Figure 11:
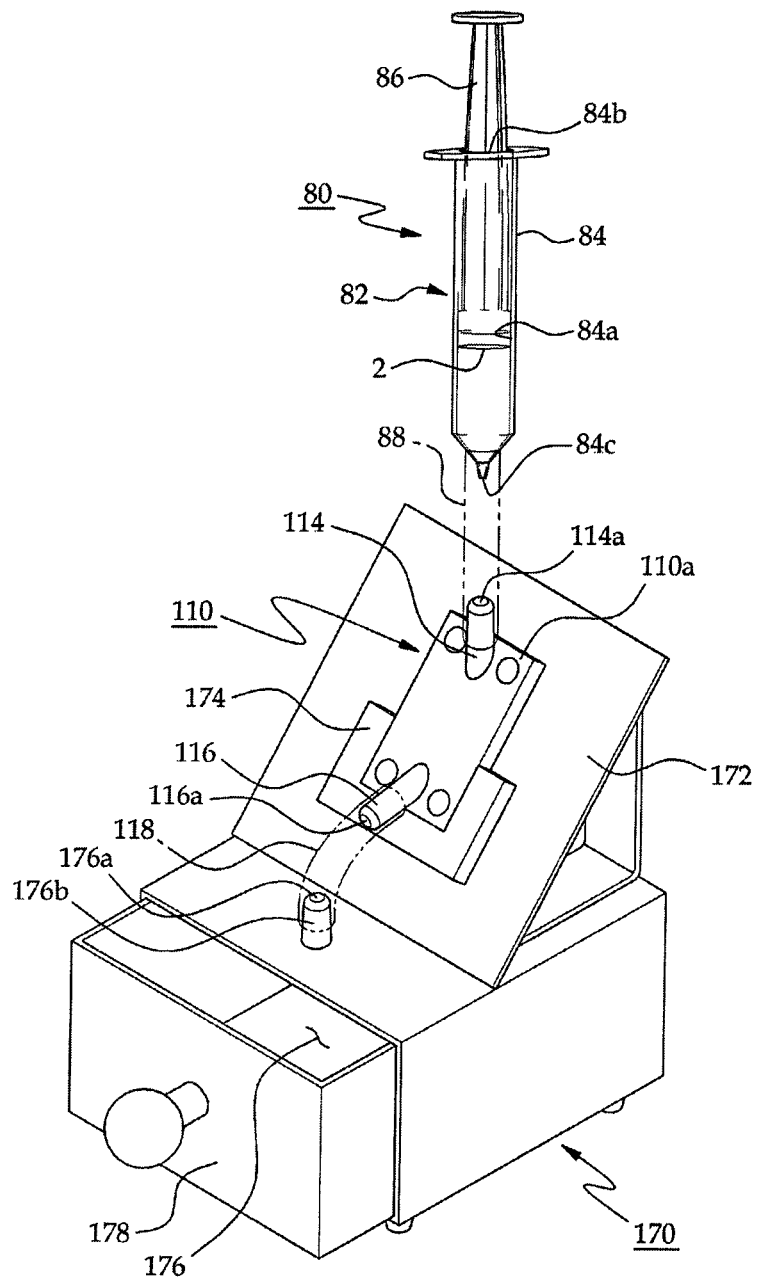
FIG. 11 is a perspective view showing a micro-fluidic device according to a second embodiment of the present invention.
Figure 12:
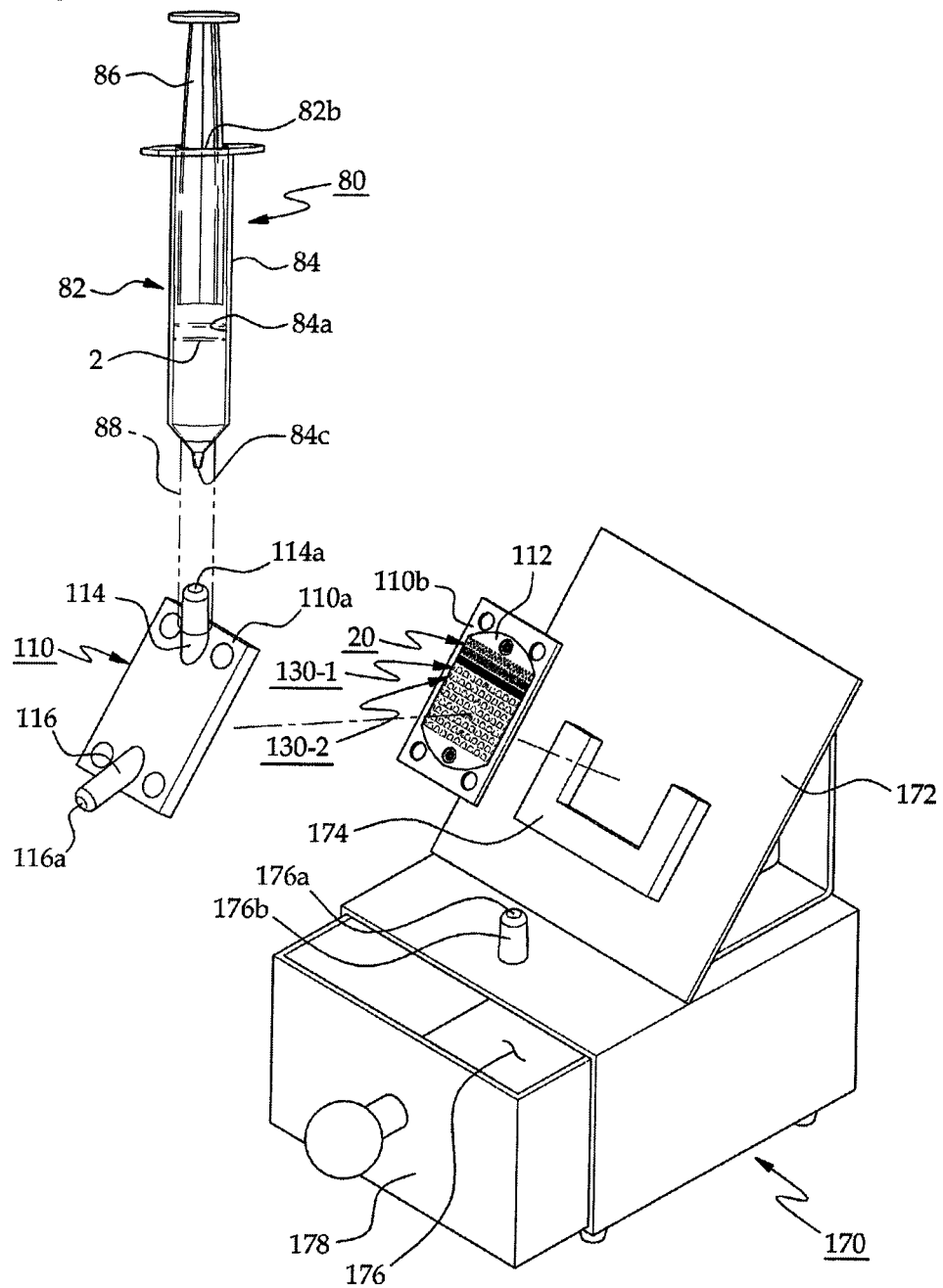
FIG. 12 is a perspective view showing a filter case in an exploded state in the micro-fluidic device according to the second embodiment of the present invention.
Figure 13:
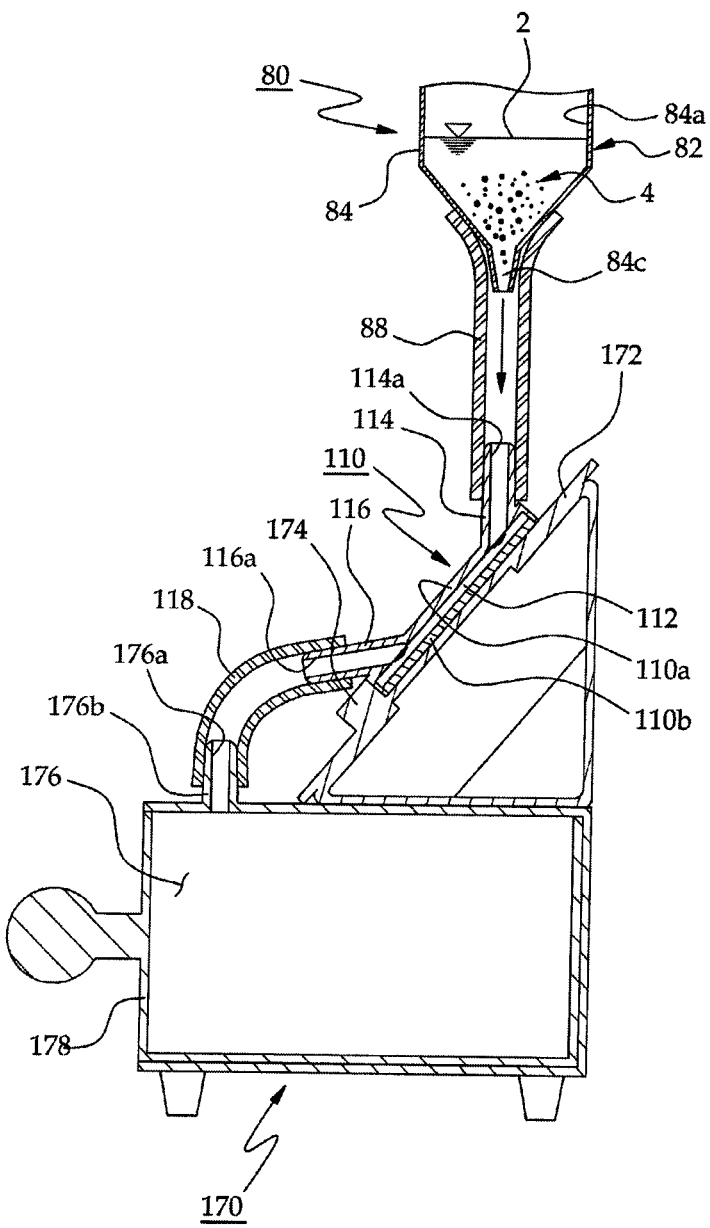
FIG. 13 is a section view showing the configuration of the micro-fluidic device according to the second embodiment of the present invention.

Referring to FIGS. 11 through 13, the micro-fluidic device according to the second embodiment includes a filter case 110 making up an outer shell. The filter case 110 includes an upper case part 110a and a lower case part 110b attached to the rear surface of the upper case part 110a to define a channel 112 between the upper case part 110a and the lower case part 110b. A first nipple 114 having an inlet 114a for the introduction of a sample 2 is connected to the upstream portion of the channel 112. A second nipple 116 having an outlet 116a for the discharge of the sample 2 is connected to the downstream portion of the channel 112. The first and second nipples 114 and 116 protrude from the upper and lower portions of the front surface of the filter case 110.

Figure 14:
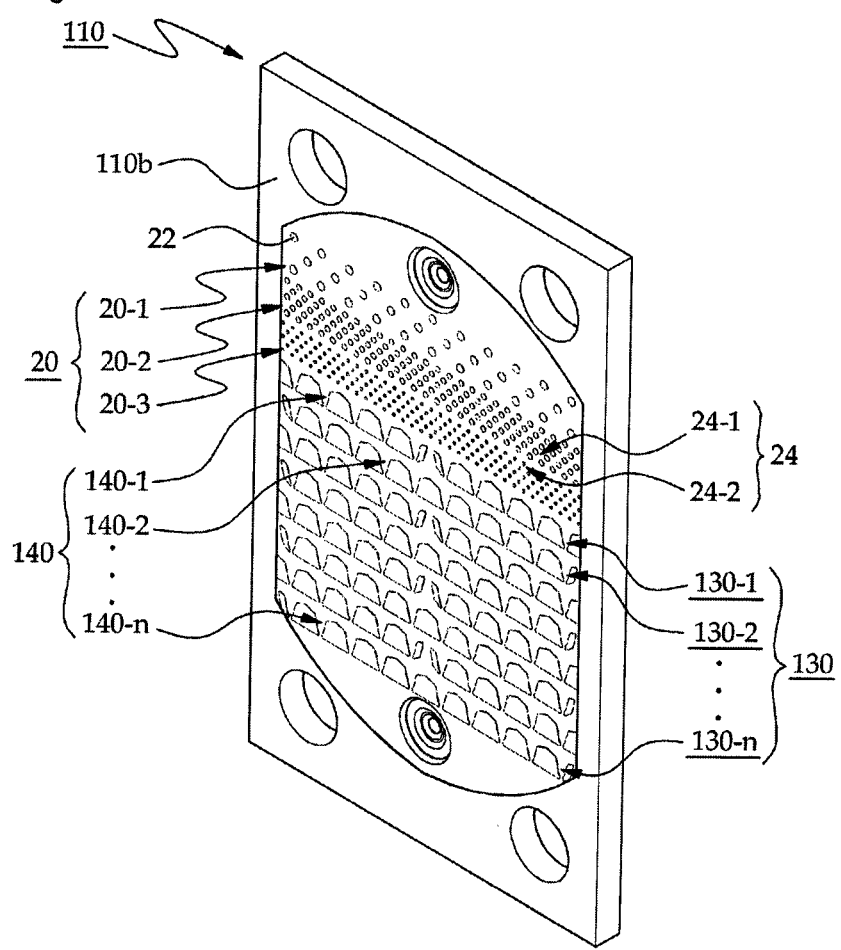
FIG. 14 is a perspective view showing a lower case part of a filter case employed in the micro-fluidic device according to the second embodiment of the present invention, with an upper case part removed for clarity.
Figure 15:
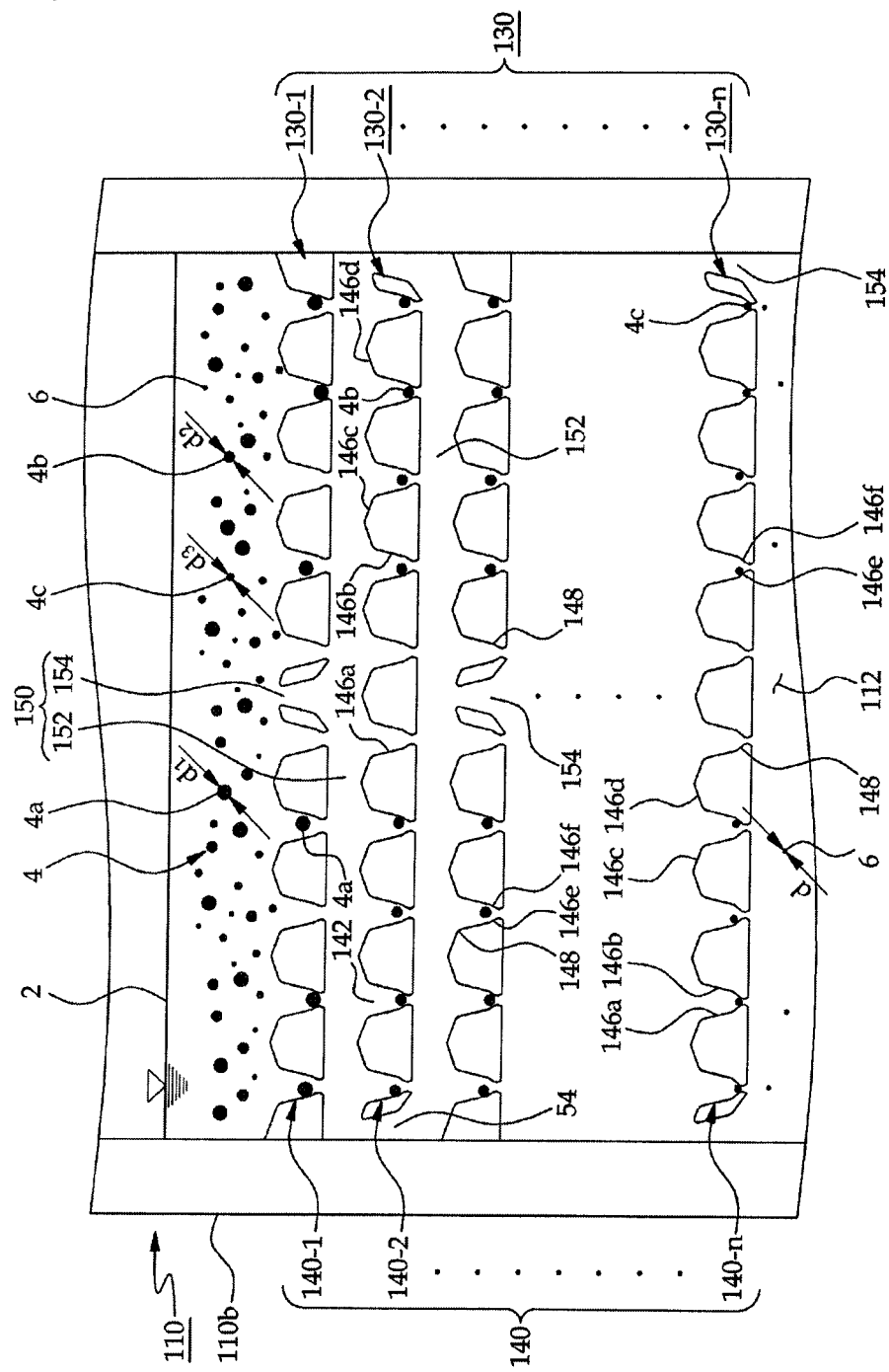
FIG. 15 is a front view showing the configuration of capture arrays in the micro-fluidic device according to the second embodiment of the present invention.

Referring to FIGS. 12, 14 and 15, the micro-fluidic device according to the second embodiment includes a plurality of capture arrays 130 (130-1 through 130-n) arranged at the downstream side of the dispersing units 20 in a spaced-apart relationship along the flow direction of the sample 2 so as to capture targets 4 contained in the sample 2. Each of the capture arrays 130 includes a plurality of funnels 140 (140-1 through 140-n) arranged along the direction orthogonal to the flow direction of the sample 2. Each of the funnels 140 has an entrance 142 arranged at the upstream side of the channel 112 along the flow direction of the sample 2 and an exit 144 at the downstream side of the channel 112 along the flow direction of the sample 2. The cross-sectional area of each of the funnels 140 is gradually reduced from the entrance 142 toward the exit 144. The funnels 140 are arranged such that the cross-sectional areas of the exits 144 of the funnels 140 are gradually reduced along the flow direction of the sample 2.

Figure 17:
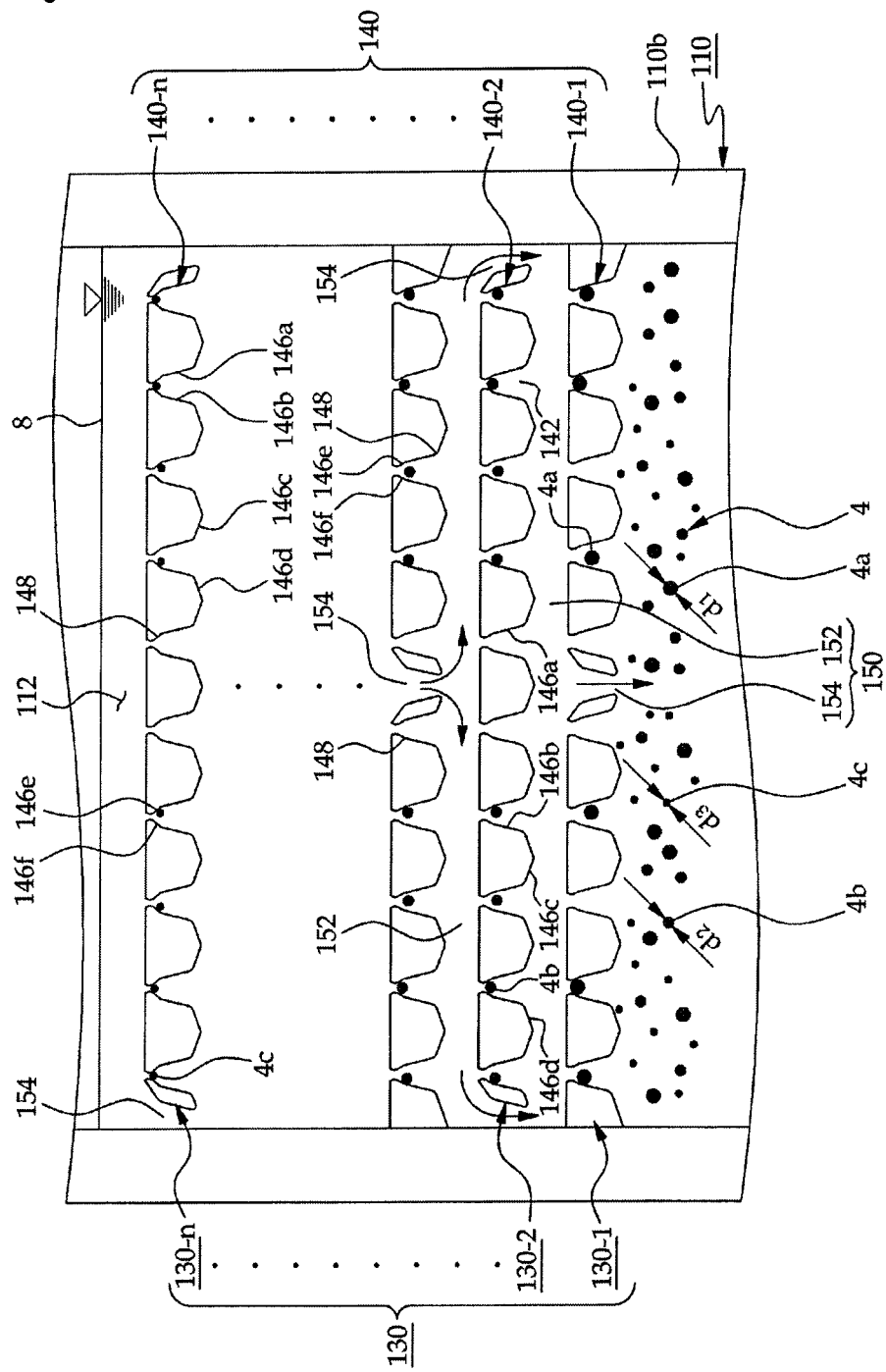
FIG. 17 is a front view for explaining how to separate targets from the capture arrays in the micro-fluidic device according to the second embodiment of the present invention.

Referring to FIGS. 15 and 17, a discharge path 150 is formed between the capture arrays 130. The discharge path 150 serves as a reverse flow guide means for guiding the flow of different kinds of targets 4 captured by the funnels 140 in the direction opposite to the flow direction of the sample 2. The discharge path 150 includes a plurality of horizontal paths 152 formed between the capture arrays 130 and a plurality of vertical paths 154 formed between the funnels 140 so as to interconnect the horizontal paths 152. The vertical paths 154 are connected to the horizontal paths 152 in a zigzag pattern.

Referring again to FIGS. 11 through 13, the micro-fluidic device according to the second embodiment includes a stand 170. The stand 170 includes a slant table 172 on which the filter case 110 can be obliquely placed and a holder 174 to which the edge of the filter case 110 can be fitted. A space 176 for receiving the sample 2 is formed within the stand 170. A nipple 176b having an introduction hole 176a for introducing the sample 2 discharged through the outlet 116a of the filter case 110 into the space 176 is formed on the upper surface of the stand 170. A container 178 is provided to receive the sample 2 introduced into the space 176 of the stand 170. The introduction hole 176a is arranged above the container 178. The container 178 can be slid into and out of the space 176 like a drawer.

The first nipple 114 of the filter case 110 is connected to the syringe 82 of the sample supply unit 80 by means of a hose 88. The second nipple 116 of the filter case 110 is connected to the nipple 176b of the stand 170 by means of a hose 118. The sample 2 is introduced from the syringe 82 into the space 176 through the hose 88, the inlet 114a, the channel 112, the outlet 116a, the hose 118 and the introduction hole 176a. Then, the sample 2 is received in the container 178.

Figure 16:
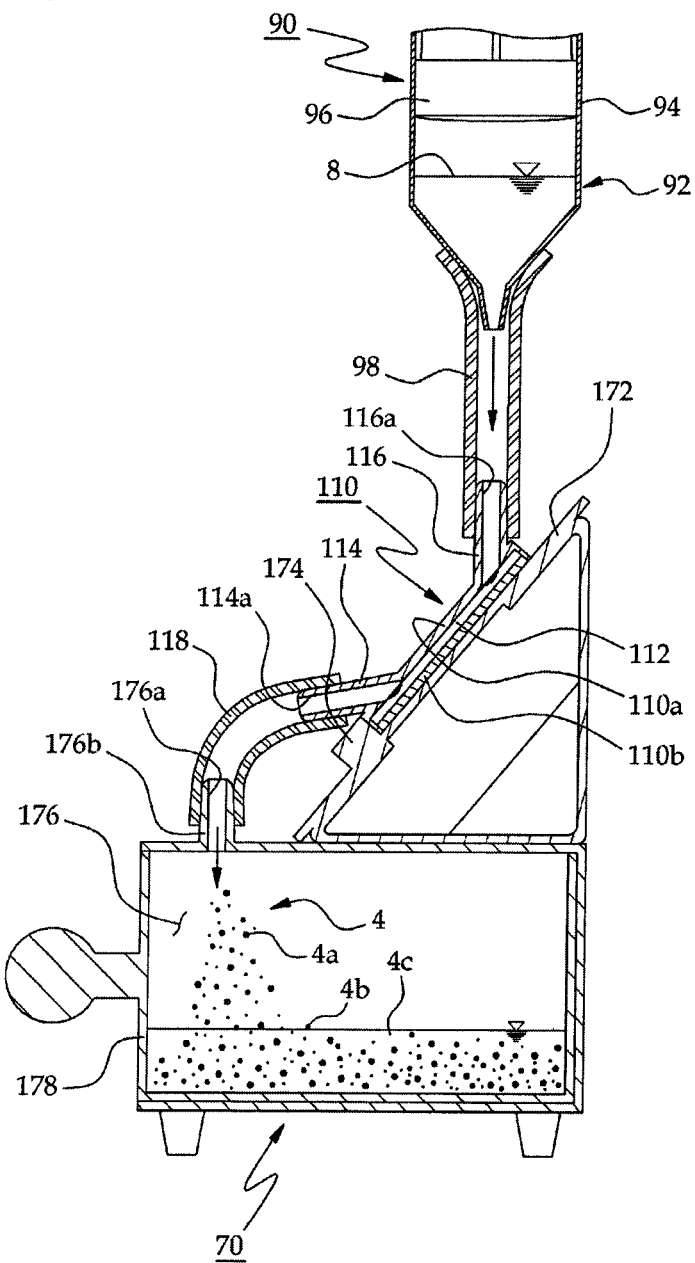
FIG. 16 is a section view of the micro-fluidic device according to the second embodiment of the present invention, showing the filter case attached to the stand in a 180 degree rotated state.

As shown in FIG. 16, if the filter case 110 is fitted to the holder 174 in a 180 degree rotated state so that the first nipple 114 of the filter case 110 can face downward with the second nipple 116 facing upward, the first nipple 114 is connected to the nipple 176b of the stand 170 by means of the hose 118. The solution 8 supplied from the syringe 92 of the carrier fluid supply unit 90 is introduced into the space 176 through the hose 98, the outlet 116a, the channel 112, the inlet 114a, the hose 118 and the introduction hole 176a. Then, the solution 8 is received in the container 178.

With the structure in which the first nipple 114 or the second nipple 116 of the filter case 110 is connected to the introduction hole 176a of the stand 170 through the hose 118, it is possible to easily mount the filter case 110 to the holder 174 in a 180 degree rotated state. If necessary, the filter case 110 and the stand 170 of the micro-fluidic device according to the second embodiment may be applied to the filter case 10 and the stand 70 of the micro-fluidic device according to the first embodiment.

Description will now be made on the operation of the micro-fluidic device according to the second embodiment of the present invention.

Referring to FIGS. 11 through 14, the sample 2 is introduced into the upstream portion of the channel 112 through the hose 188 and the inlet 114a of the filter case 110. Thereafter, the sample 2 is dispersed in the direction orthogonal to the flow direction of the sample 2 while passing through between the posts 22 of the first to third dispersing units 20-1, 20-2 and 20-3.

As shown in FIG. 15, the sample 2 flows down from the entrances 142 of the funnels 140 toward the exits 144 thereof. The sample 2 passes through the first funnels 140-1 of the first capture arrays 130-1. The first funnels 140-1 capture the first kind targets 4a. The second funnels 140-2 of the second capture arrays 130-2 capture the second kind targets 4b. The last funnels 140-n of the last capture arrays 130-n capture the third kind targets 4c. The non-targets 6 pass through all the capture arrays 130. The sample 2 and the non-targets 6 are introduced into the space 176 through the outlet 116a of the filter case 110 and the introduction hole 176a of the stand 170 and are received in the container 178.

Referring to FIGS. 16 and 17, the targets 4 captured by the capture arrays 130 are separated and collected by a target separating method using the micro-fluidic device according to the second embodiment of the present invention. In order to collect the targets 4, the filter case 110 is fitted to the holder 174 by 180 degree rotating the filter case 110 so that the inlet 114a can face downward with the outlet 116a facing upward. If the filter case 110 is attached to the slant table 172 in a 180 degree rotated state, the entrances 142 of the funnels 140 are arranged at the downstream side of the channel 112 with the exits 144 arranged at the upstream side of the channel 112. Thus the funnels 140 are oriented in the direction opposite to the filtering direction.

Upon operating the syringe 92, the solution 8 is introduced into the channel 112. Then, the solution 8 flows down from the exits 144 of the funnels 140 toward the entrances 142 thereof. As a consequence, the targets 4 captured by the funnels 140 flow out of the entrances 142 and then flow down toward the inlet 114a of the filter case 110. The targets 4 flowing in the direction opposite to the capturing direction can smoothly pass through the discharge path 150 formed between the capture arrays 130. Along with the flow of the solution 8, the targets 4 pass through the dispersing units 20, the inlet 114a of the filter case 110 and the introduction hole 176a of the stand 170 in the named order and then flow into the space 176. The targets 4 and the solution 8 flowing into the space 176 are received in the container 178.

Figure 18:
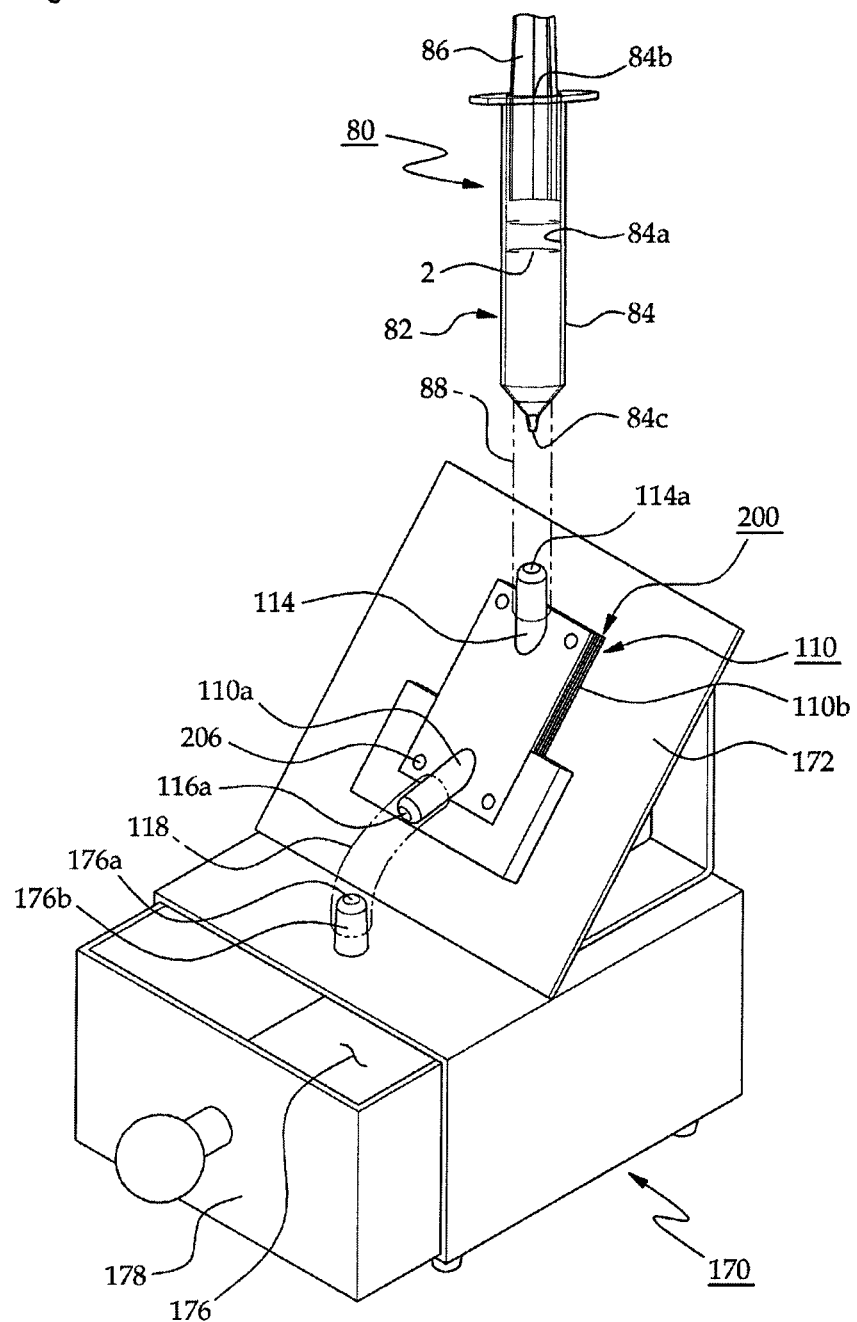
FIG. 18 is a perspective view showing the configuration of a micro-fluidic device according to a third embodiment of the present invention.
Figure 19:
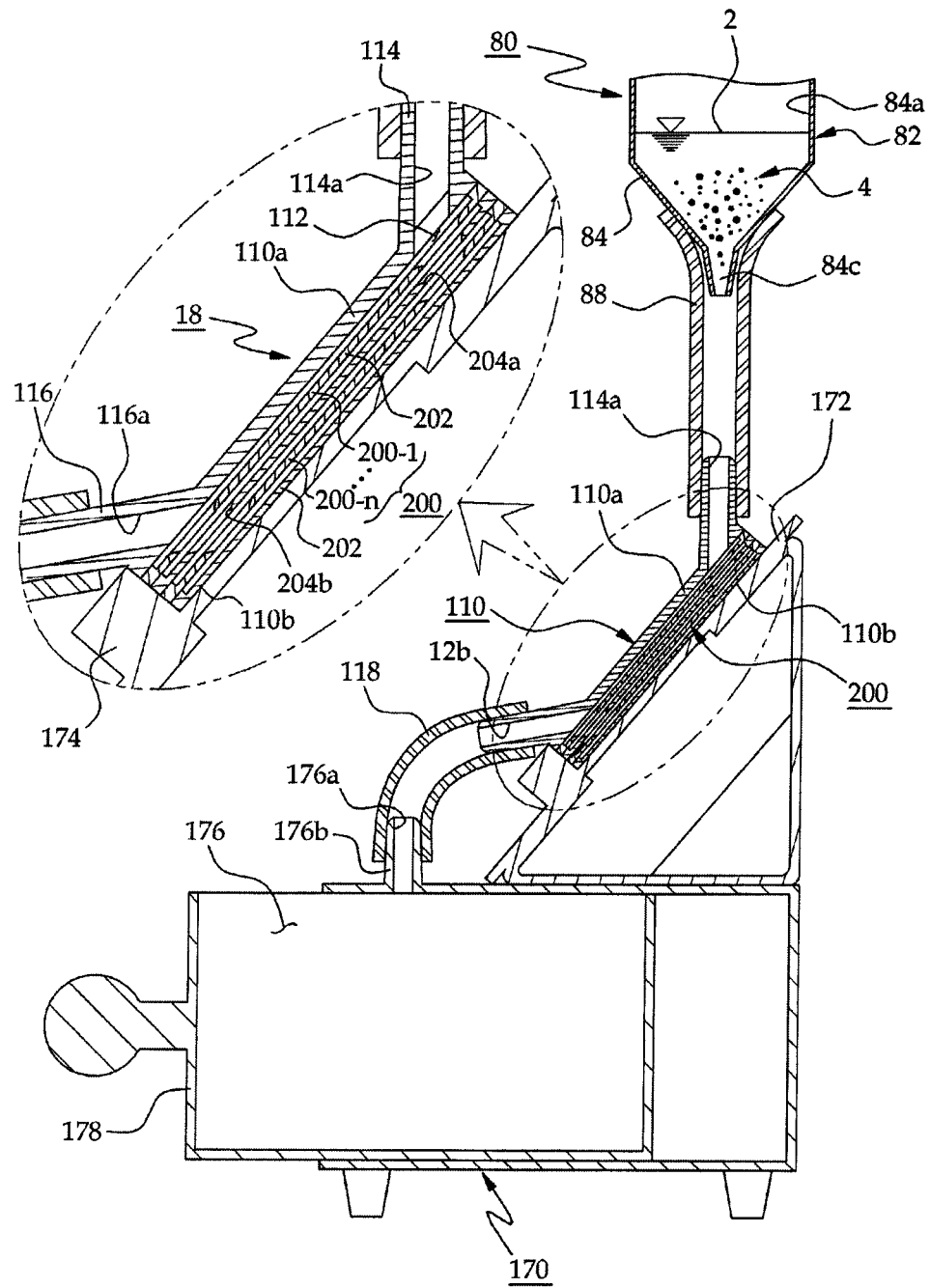
FIG. 19 is a section view showing the configuration of the micro-fluidic device according to the third embodiment of the present invention.
Figure 20:
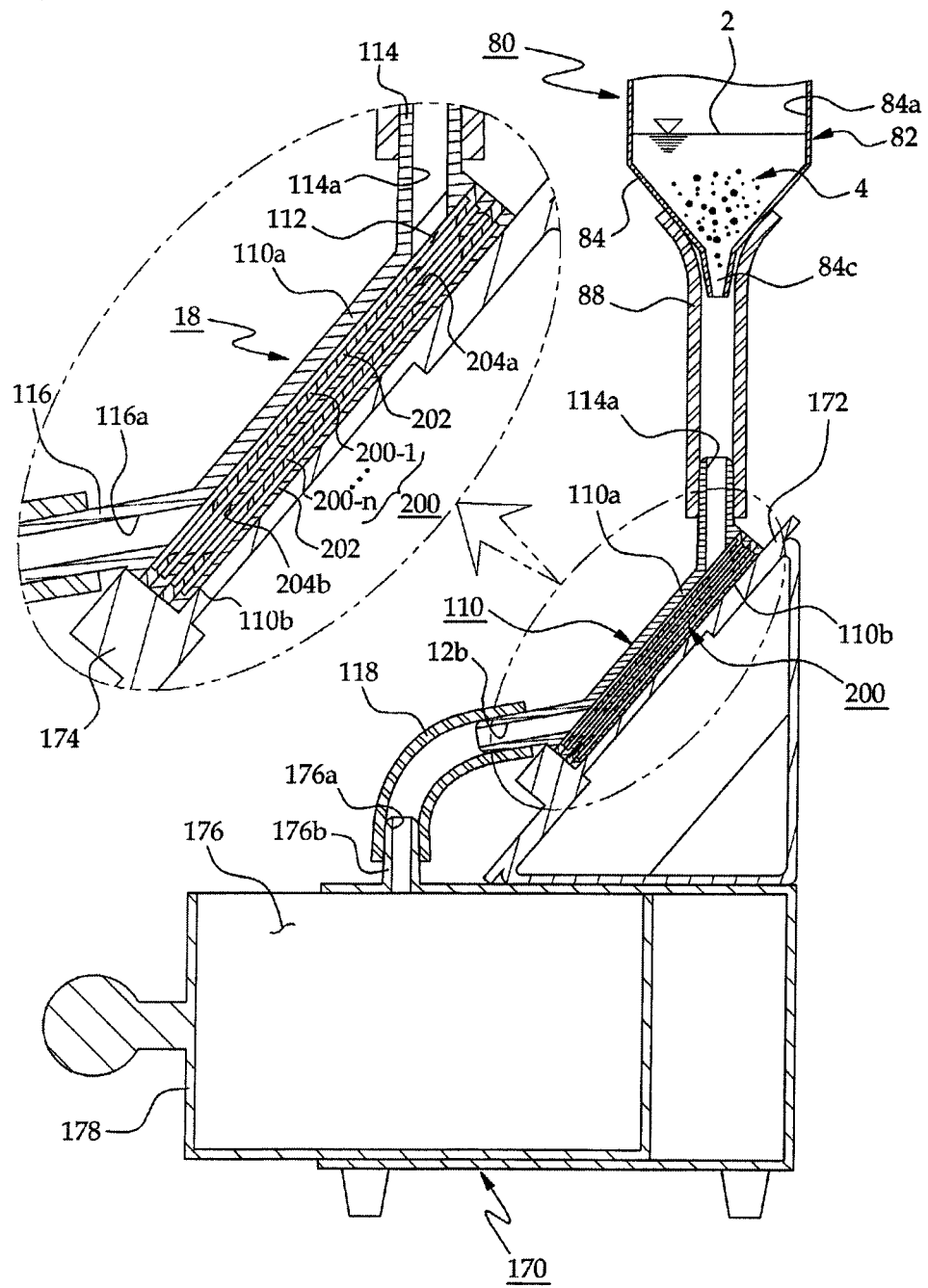
FIG. 20 is a perspective view showing the configuration of partition plates in the micro-fluidic device according to the third embodiment of the present invention, with an upper case part removed for clarity.

FIGS. 18 through 24 show a micro-fluidic device according to a third embodiment of the present invention. Referring to FIGS. 18 and 19, the micro-fluidic device according to the third embodiment includes a filter case 110 and a stand 170 which have the same configuration as the filter case 110 and the stand 170 of the micro-fluidic device according to the second embodiment. Therefore, no description will be made on the configuration and operation of the filter case 110 and the stand 170. In addition, the micro-fluidic device according to the third embodiment includes a dispersing units 20, first and second capture arrays 30-1 and 30-2, a sample supply unit 80 and a carrier fluid supply unit 90 which have the same configuration as the dispersing units 20, the first and second capture arrays 30-1 and 30-2, the sample supply unit 80 and the carrier fluid supply unit 90 of the micro-fluidic device according to the first embodiment. Therefore, no description will be made on the configuration and operation thereof.

Referring to FIGS. 18 through 21, the micro-fluidic device according to the third embodiment includes a filter case 110 having an upper case part 110a and a lower case part 110b, and a plurality of partition plates 200 (200-1 through 200-n) arranged between the upper case part 110a and the lower case part 110b. The partition plates 200 are stacked between the upper case part 110a and the lower case part 110b so as to divide the channel 112 into a plurality of sub-channels 202. A first path 204a and a second path 204b are formed in the upper and lower portions of each of the partition plates 200 so as to interconnect the sub-channels 202.

The upper case part 110a is positioned at the front side of the first partition plate 200-1, one of the partition plates 200 arranged in the most front position, so as to cover the sub-channel 202 of the first partition plate 200-1. The lower case part 110b is positioned at the rear side of the last partition plate 200-n, one of the partition plates 200 arranged in the most rear position. The case 110 and the partition plates 200 are fastened together by a plurality of screws 206. Each of the lower case part 110b and the partition plates 200 includes dispersing units 20, first capture arrays 30-1 and second capture arrays 30-2 arranged on the front surface thereof.

Figure 22:
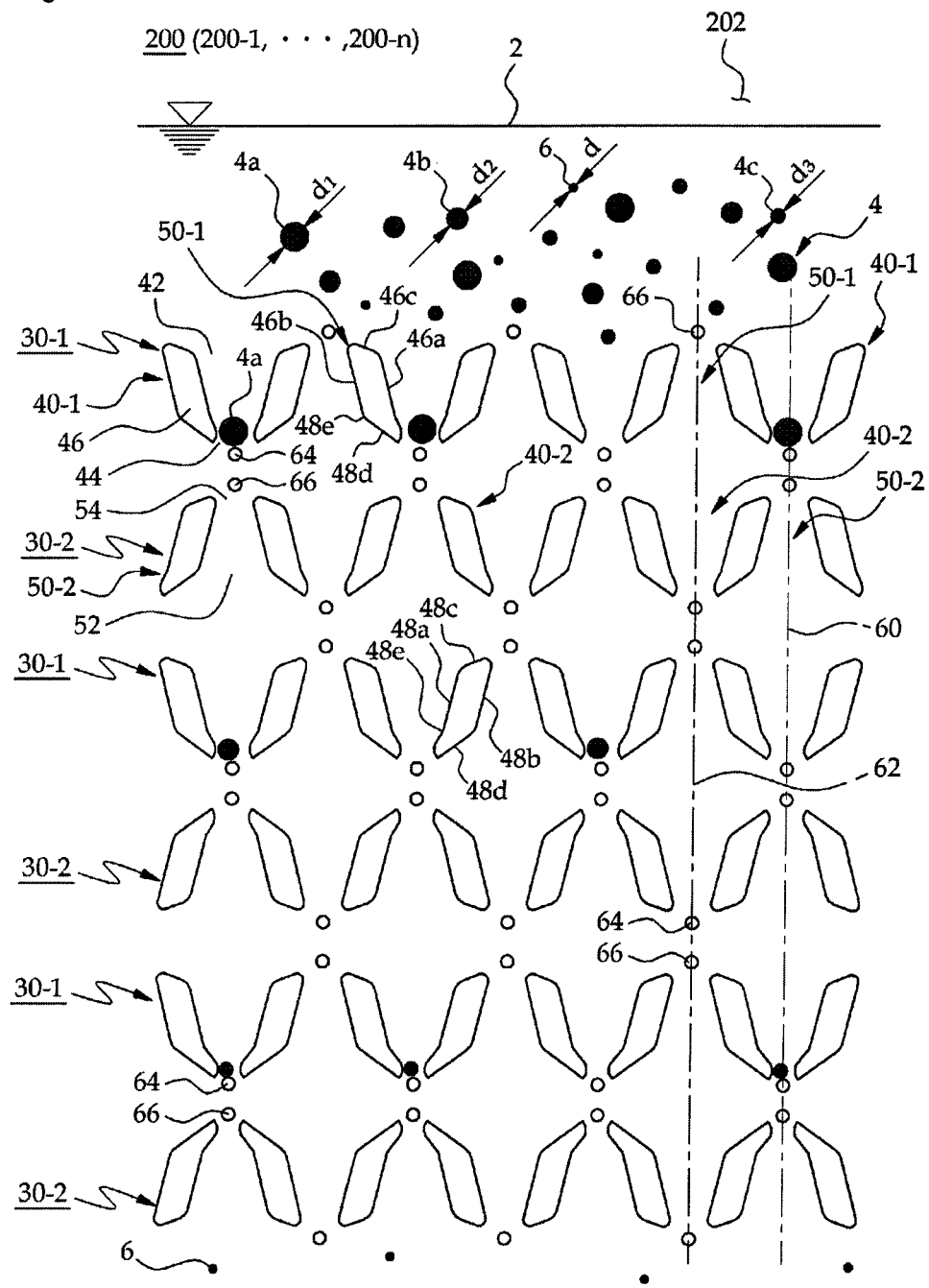
FIG. 22 is a front view showing the configuration of first and second capture arrays in the micro-fluidic device according to the third embodiment of the present invention.
Figure 23:
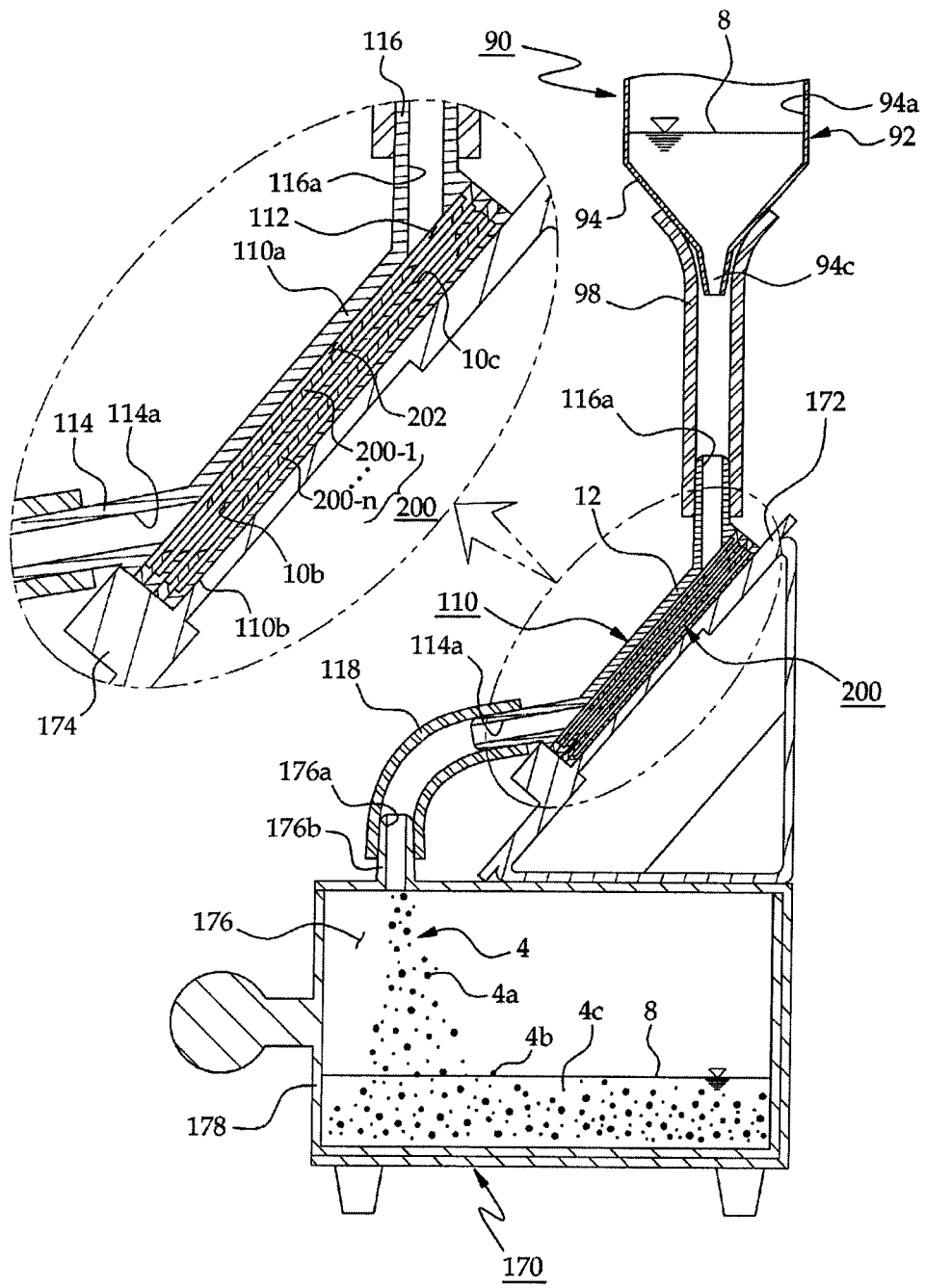
FIG. 23 is a section view showing a filter case installed on a stand in a 180 degree rotated state in the micro-fluidic device according to the third embodiment of the present invention.
Figure 24:
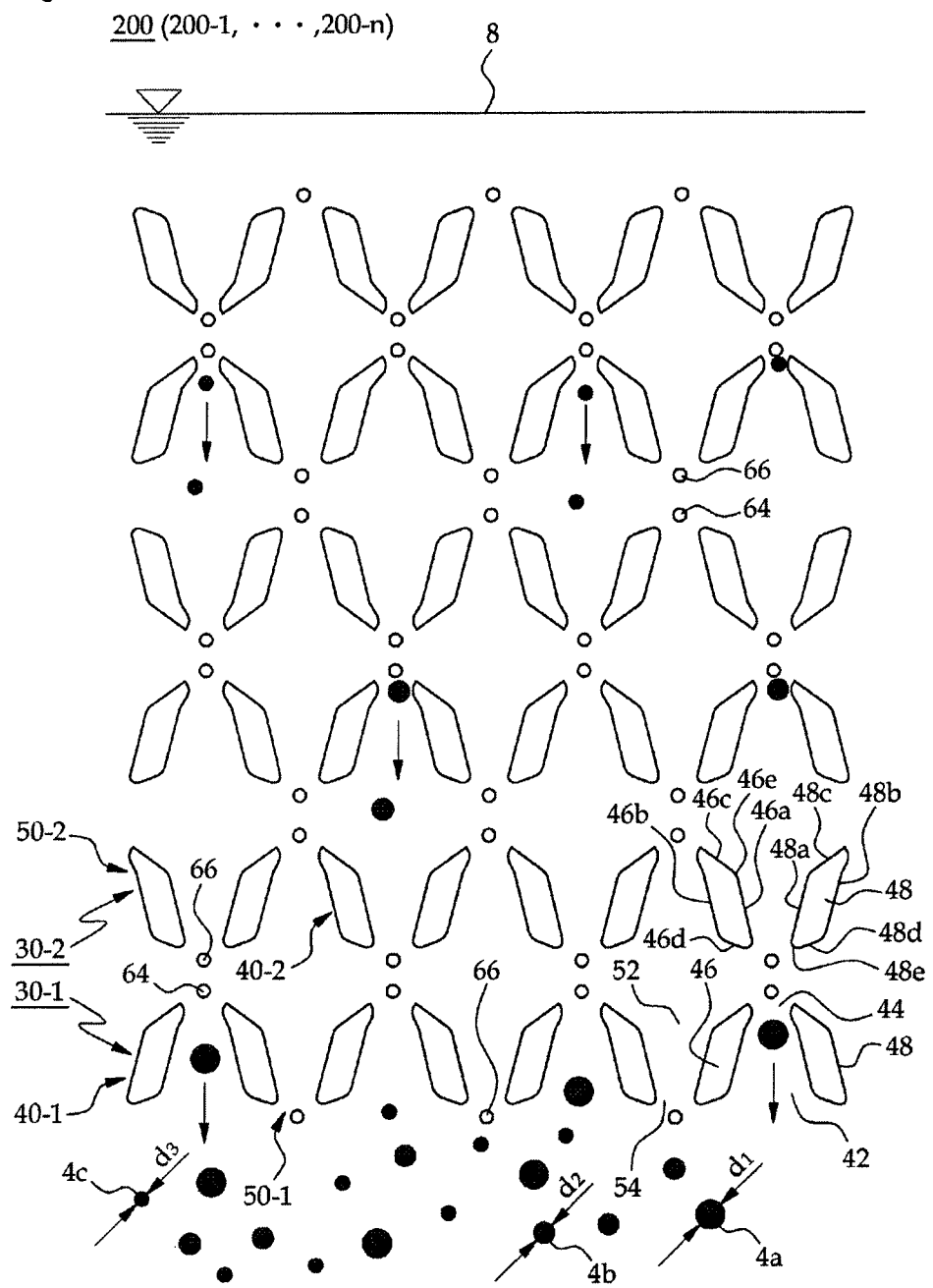
FIG. 24 is a front view for explaining how to separate targets from the first and second capture arrays in the micro-fluidic device according to the third embodiment of the present invention.
Figure 25:
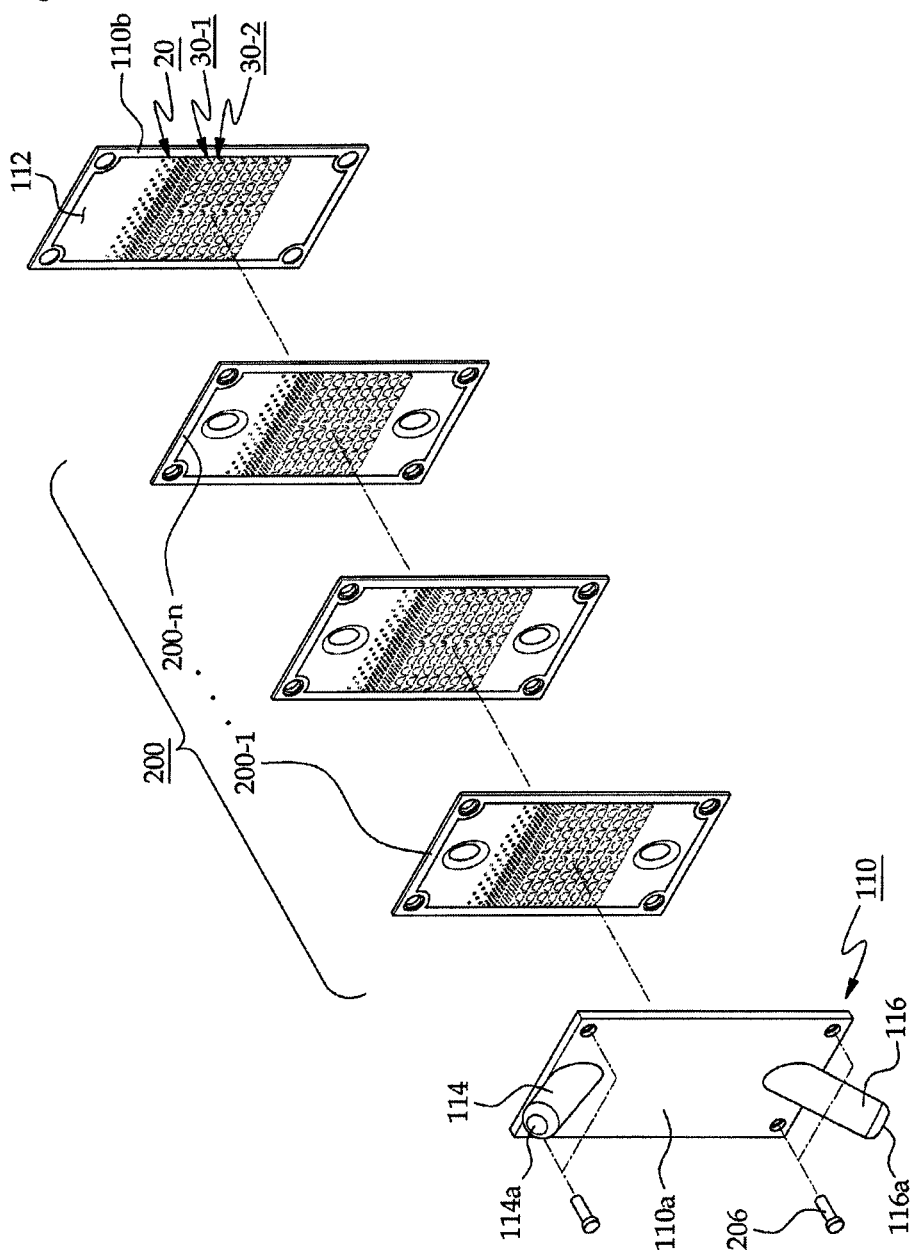
FIG. 25 is a perspective view showing the filter case and the partition plates in an exploded state in a micro-fluidic device according to a fourth embodiment of the present invention.
Figure 26:
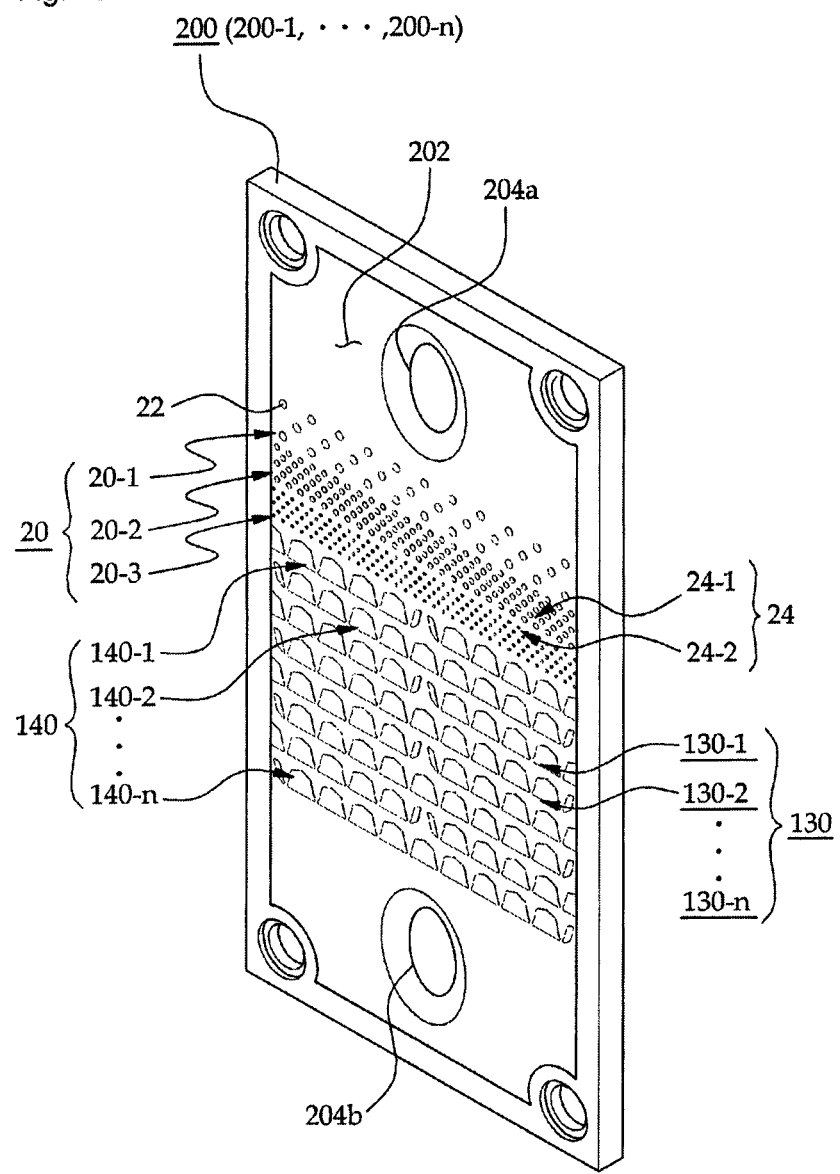
FIG. 26 is a perspective view showing one of the partition plates employed in the micro-fluidic device according to the fourth embodiment of the present invention.
Figure 27:
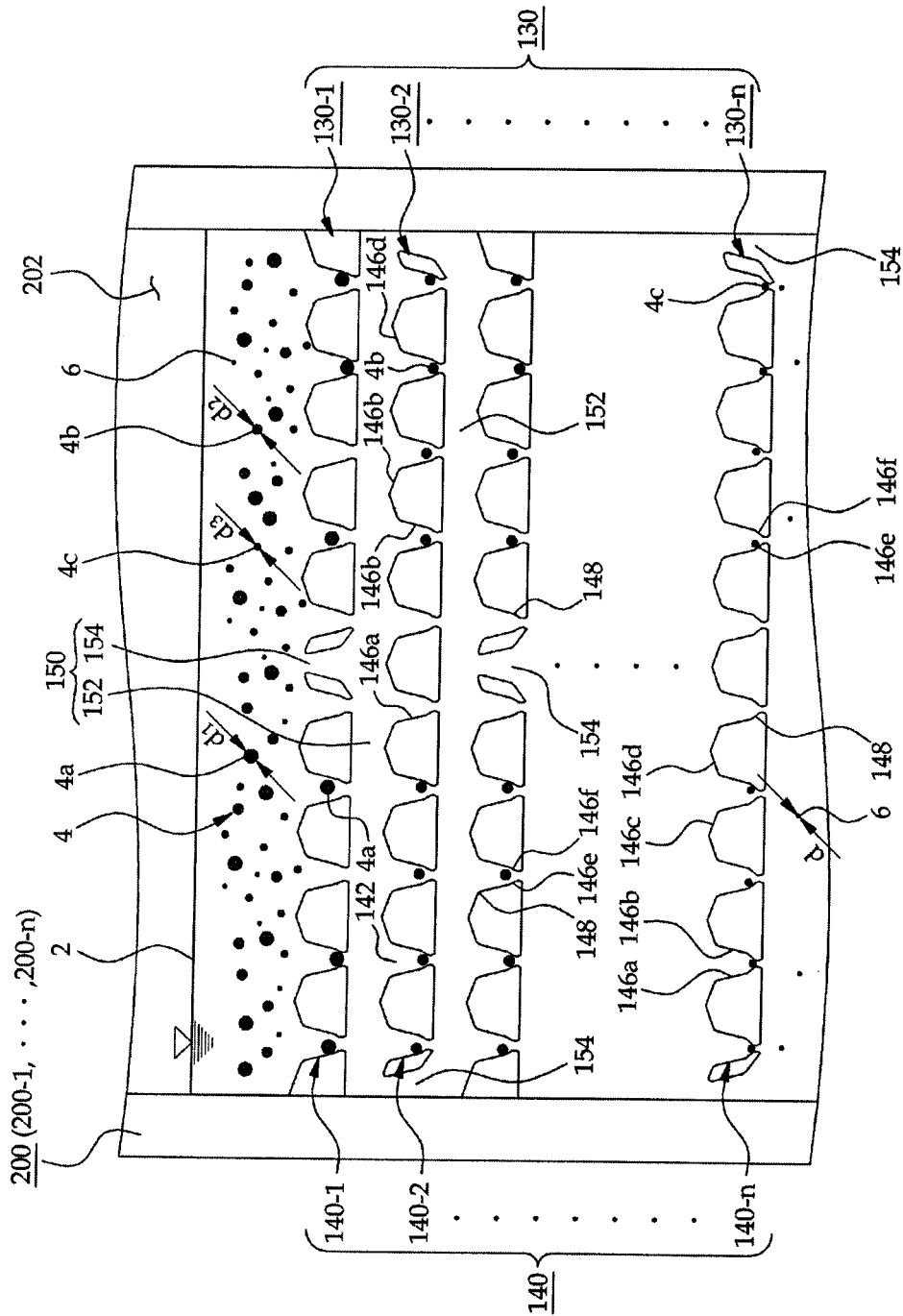
FIG. 27 is a front view showing the capture arrays employed in the micro-fluidic device according to the fourth embodiment of the present invention.

Referring to FIGS. 18, 19 and 22, the sample 2 is introduced into the upstream portion of the sub-channel 202 of the first partition plate 200-1 through the hose 188 and the inlet 114a of the filter case 110. The sample 2 introduced into the sub-channel 202 of the first partition plate 200-1 flows toward the sub-channels 202 of the partition plates 200 through the first paths 204a of the partition plates 200.

As shown in FIG. 22, the sample 2 is dispersed in the direction orthogonal to the flow direction of the sample 2 while passing through between the posts 22 of the first to third dispersing units 20-1, 20-2 and 20-3. The sample 2 flows down from the entrances 42 of the first funnels 40-1 toward the exits 44 thereof. The first kind targets 4a are captured by the first funnels 140 40-1. The sample 2 passed through the first funnels 40-1 flows down from the entrances 42 of the second funnels 40-2 toward the exits 44 thereof. The second kind targets 4b are captured by the second funnels 40-2. The third kind targets 4c are captured by the first capture arrays 30-1 or the second capture arrays 30-2 arranged in multiple stages. The non-targets 6 can pass all the first and second capture arrays 30-1 and 30-2.

After passing through the first and second capture arrays 30-1 and 30-2, the sample 2 and the non-targets 6 flow into the sub-channel 202 of the first partition plate 200-1 through the second paths 204b of the partition plates 200. The sample 2 and the non-targets 6 flow from the sub-channel 202 of the first partition plate 200-1 into the space 176 through the outlet 116a and the introduction hole 176a of the stand 170. Then, the sample 2 and the non-targets 6 are received in the container 178.

With the structure in which a large quantity of sample 2 is divisionally supplied to the sub-channels 202 of the partition plates 200 and in which the targets 4 are captured by the first and second capture arrays 30-1 and 30-2, it is possible to shorten the time required in treating the sample 2. Since the targets 4 are filtered and separated on a size-by-size basis by the first and second capture arrays 30-1 and 30-2 arranged in multiple stages, it is possible to efficiently collect, e.g., white blood cells from the human blood.

Figure 21:
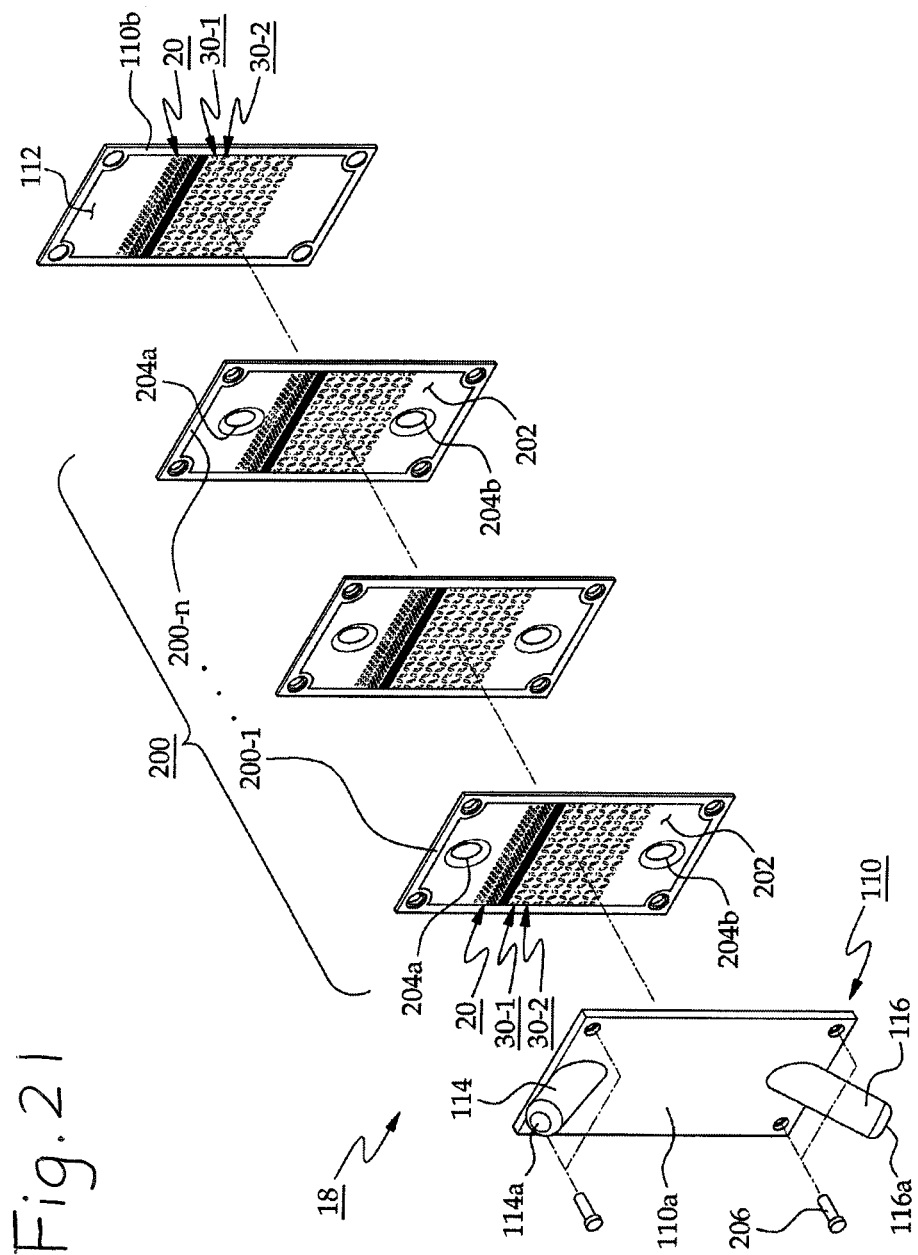
FIG. 21 is a perspective view showing the filter case and the partition plates in an exploded state in the micro-fluidic device according to the third embodiment of the present invention.

Referring to FIGS. 21 and 22, the targets 4 are separated and collected from the first and second capture arrays 30-1 and 30-2 by a target separating method using the micro-fluidic device according to the third embodiment of the present invention. In order to collect the targets 4, the filter case 110 is fitted to the holder 174 by 180 degree rotating the filter case 110 so that the inlet 114a can face downward with the outlet 116a facing upward. The inlet 114a is connected to the introduction hole 176a of the stand 170.

The outlet 116a of the filter case 110 is connected to the cylinder 94 by the hose 98. Thereafter, the syringe 92 is operated so that the solution 8 can be introduced into the channel 112 through the hose 98 and the outlet 116a. The solution 8 is divisionally supplied to the sub-channels 202 through the second paths 204b of the partition plates 200.

Subsequently, the solution 8 flows down from the entrances 52 of the second reverse funnels 50-2 toward the exits 52 thereof. In addition, the solution 8 flows down from the exits 44 of the second forward funnels 40-2 toward the entrances 42 thereof. As a consequence, the targets 4 captured by the second forward funnels 40-2, e.g., the second kind targets 4b, flow out of the entrances 42 of the second forward funnels 40-2 and flow toward the first capture arrays 30-1 along the channel 112.

Thereafter, the targets 4 flow into the first reverse funnels 50-1 through the entrances 52 of the first reverse funnels 50-1 and then flow toward the exits 54. The targets flowing in the direction opposite to the capturing direction can easily pass through between the exits 54 and the second obstruction bodies 66. The second kind targets 4b passed through the exits 54 of the first reverse funnels 50-1 and the first kind targets 4a captured by the first forward funnels 40-1 flow, together with the solution 8, through the third dispersing unit 20-3, the second dispersing unit 20-2, the first dispersing unit 20-1, the first paths 204a, the inlet 114a and the introduction hole 176a in the named order. Then, the second kind targets 4b and the first kind targets 4a are introduced into the space 176. The targets 4 and the solution 8 introduced into the space 176 are received in the container 178. The container 178 is then opened and the targets 4 received in the container 78 are collected.

FIGS. 25 through 28 show a micro-fluidic device according to a fourth embodiment of the present invention. Referring to FIGS. 25 through 28, the micro-fluidic device according to the fourth embodiment includes a filter case 110 and a plurality of partition plates 200 (201-1 through 201-n) which have the same configuration as the filter case 110 and the partition plates 200 (201-1 through 201-n) of the micro-fluidic device according to the third embodiment. Therefore, no detailed description will be made on the configuration and operation of the filter case 110 and the partition plates 200 (201-1 through 201-n). In addition, the micro-fluidic device according to the fourth embodiment includes a plurality of dispersing units 20 (20-1, 20-2 and 20-3), a plurality of capture arrays 130 (130-1 through 130-n) and a discharge path 150 which have the same configuration as the dispersing units 20 (20-1, 20-2 and 20-3), the capture arrays 130 (130-1 through 130-n) and the discharge path 150 of the micro-fluidic device according to the second embodiment. Therefore, no detailed description will be made on the configuration and operation of the dispersing units 20 (20-1, 20-2 and 20-3), the capture arrays 130 (130-1 through 130-n) and the discharge path 150.

In the micro-fluidic device according to the fourth embodiment, each of the partition plates 200 and the lower case part 110b includes a plurality of dispersing units 20 (20-1, 20-2 and 20-3), a plurality of capture arrays 130 (130-1 through 130-n) and a discharge path 150 formed on the front surface thereof. Upon operating the syringe 82, the sample 2 is introduced into the channel 112 and is then divisionally supplied to the sub-channels 202 through the first paths 204a of the partition plates 200. The sample 2 is dispersed in the direction orthogonal to the flow direction of the sample 2 while passing through between the posts 22 of the first to third dispersing units 20-1, 20-2 and 20-3. The targets 4 are captured by the funnels 140 of the capture arrays 130. The non-targets 6 can pass all the capture arrays 130.

Figure 28:
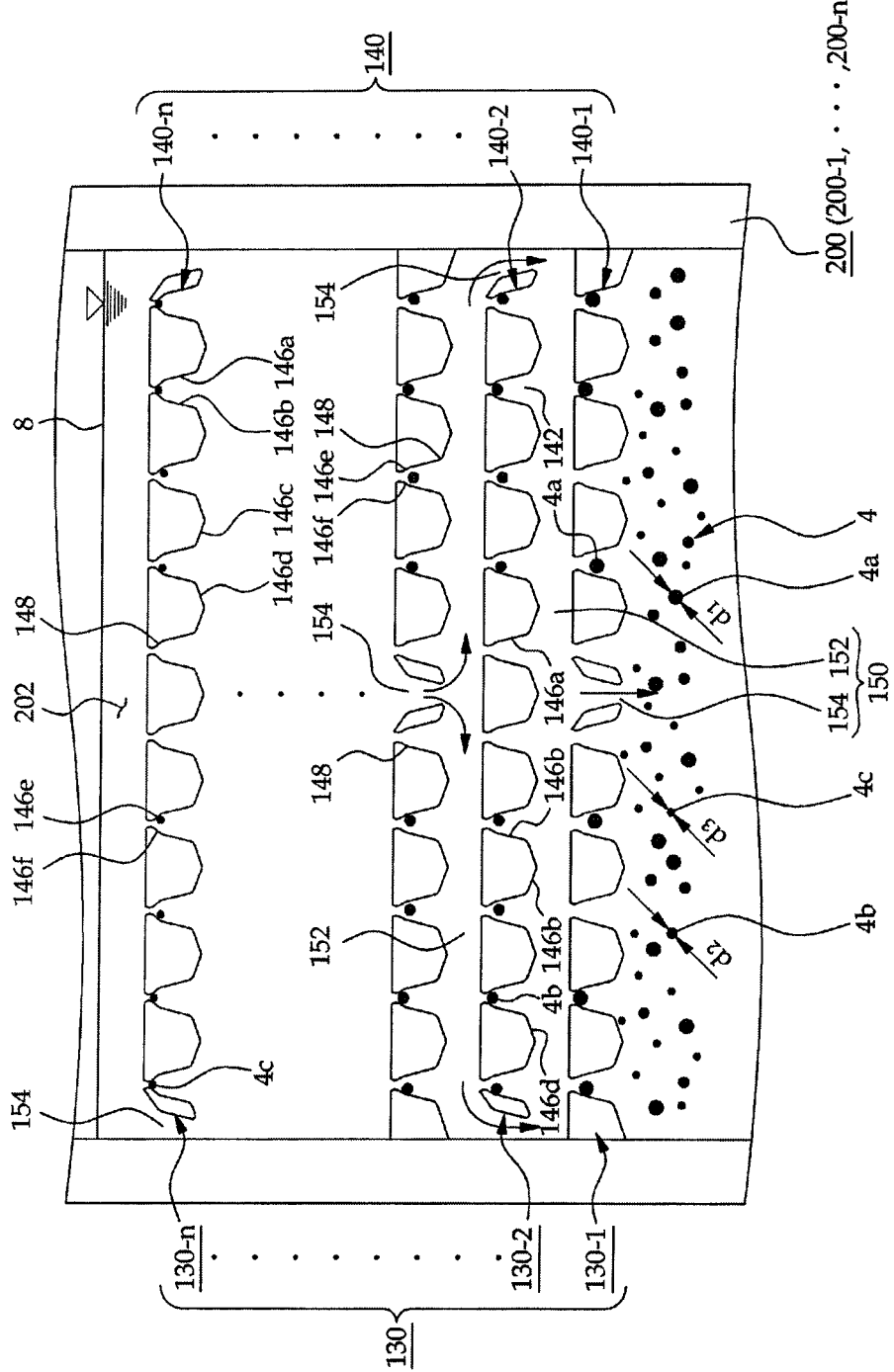
FIG. 28 is a front view for explaining how to separate targets from the capture arrays in the micro-fluidic device according to the fourth embodiment of the present invention.

As shown in FIG. 28, if the funnels 140 are 180 degree rotated to face in the direction opposite to the capturing direction of the targets 4, the solution 8 flows down from the exits 144 of the funnels 140 toward the entrances 142. As a consequence, the targets 4 captured by the funnels 140 flow out of the entrances 142 and flow along the sub-channels 202 and the discharge path 150. Then, the targets 4 are discharged out of the filter case 110 through the first paths 204a and the inlet 114a. The targets 4 flowing in the direction opposite to the capturing direction can smoothly pass through the discharge path 150 formed between the capture arrays 130.

While certain preferred embodiments of the invention have been described above, the scope of the present invention is not limited to these embodiments. It will be apparent to those skilled in the art that various changes, modifications and substitutions may be made without departing from the scope of the invention defined in the claims. Such changes, modifications and substitutions shall be construed to fall within the scope of the present invention.

What is claimed is:

1. A micro-fluidic device, comprising:
   a filter case including an inlet for introducing a sample containing different kinds of targets, an outlet for discharging the sample and a channel extending between the inlet and the outlet;
   a first capture array arranged in an upstream portion of the channel, the first capture array including a plurality of first forward funnels arranged along a direction orthogonal to a flow direction of the sample so as to capture the different kinds of targets;
   a second capture array arranged in a downstream portion of the channel, the second capture array including a plurality of second forward funnels arranged along the direction orthogonal to the flow direction of the sample so as to capture the different kinds of targets;
   a reverse flow guide configured to cause the different kinds of targets captured in the first and second forward funnels to flow toward the inlet in the direction opposite to the flow direction of the sample when the filter case is mounted in an overturned state.

2. The micro-fluidic device of claim 1, wherein the reverse flow guide includes: a plurality of first reverse funnels alternately arranged with respect to the first forward funnels; and a plurality of second reverse funnels alternately arranged with respect to the second forward funnels.

3. The micro-fluidic device of claim 2, wherein the first forward funnels and the second forward funnels are arranged in a staggering pattern.

4. The micro-fluidic device of claim 2, wherein the first forward funnels and the second reverse funnels are arranged in a coaxial relationship with each other and wherein the first reverse funnels and the second forward funnels are arranged in a coaxial relationship with each other.

5. The micro-fluidic device of claim 4, wherein each of the first forward funnels, the second forward funnels, the first reverse funnels and the second reverse funnels has an entrance and an exit, the exit of each of the first forward funnels being equal in cross-sectional area to the exit of each of the first reverse funnels, the exit of each of the second forward funnels being equal in cross-sectional area to the exit of each of the second reverse funnels.

6. The micro-fluidic device of claim 5, wherein the exit of each of the first forward funnels is larger in cross-sectional area than the exit of each of the second forward funnels and wherein the exit of each of the first reverse funnels is larger in cross-sectional area than the exit of each of the second reverse funnels.

7. The micro-fluidic device of claim 5, wherein first obstruction bodies are arranged near the exits of the first and second forward funnels so as to obstruct the different kinds of targets flowing out of the exits of the first and second forward funnels.

8. The micro-fluidic device of claim 5, wherein second obstruction bodies are arranged near the exits of the second reverse funnels so that the different kinds of targets can flow in a direction opposite to a capturing direction in which the different kinds of targets are captured by the first and second forward funnels and can flow out of the exits of the second reverse funnels.

9. The micro-fluidic device of claim 5, wherein each of the first and second forward funnels includes a first guide and a second guide provided in pair, the first guide including a first slant surface and a second slant surface obliquely extending in a parallel relationship with each other, the second guide including a first slant surface and a second slant surface obliquely extending in a parallel relationship with each other, the first slant surface of the first guide and the first slant surface of the second guide facing each other, the first guide further including a third slant surface formed at a top end thereof to obliquely extend from the second slant surface of the first guide toward the entrance of each of the first and second forward funnels, the second guide further including a third slant surface formed at a top end thereof to obliquely extend from the second slant surface of the second guide toward the entrance of each of the first and second forward funnels, the first guide further including a fourth slant surface formed at a bottom end thereof to obliquely extend from the second slant surface of the first guide toward the exit of each of the first and second forward funnels, the second guide further including a fourth slant surface formed at a bottom end thereof to obliquely extend from the second slant surface of the second guide toward the exit of each of the first and second forward funnels, the first guide further including round corners where the first through fourth slant surfaces of the first guide meet with one another, the second guide further including round corners where the first through fourth slant surfaces of the second guide meet with one another.

10. The micro-fluidic device of claim 1, wherein the reverse flow guide includes a discharge path formed between the first capture array and the second capture array so that the different kinds of targets captured by the first and second forward funnels can flow through the discharge path in the direction opposite to the flow direction of the sample.

11. The micro-fluidic device of claim 1, wherein the filter case includes an upper case part in which the inlet and the outlet are formed and a lower case part coupled to a rear surface of the upper case part to form the channel between the upper case part and the lower case part, and further comprising: a plurality of partition plates arranged in the channel to divide the channel into a plurality of sub-channels along the flow direction of the sample, each of the partition plates including a first path and a second path formed in upper and lower portions of each of the partition plates so as to interconnect the sub-channels, the lower case part attached to the last partition plate arranged in a most rear position so as to interconnect the first path and the second path of the last partition plate, the first capture array, the second capture array and the reverse flow guide arranged on a front surface of each of the partition plates and the lower case part.

12. The micro-fluidic device of claim 1, further comprising: a dispersing unit arranged between the inlet and the first capture array so as to disperse the flow of the sample.

13. The micro-fluidic device of claim 1, further comprising: a stand on which the filter case can be obliquely placed; and a sample supply unit for storing the sample and supplying the sample to the inlet.

14. A micro-fluidic device, comprising:
a filter case including an inlet for introducing a sample containing different kinds of targets, an outlet for discharging the sample and a channel extending between the inlet and the outlet;
a first capture array arranged in an upstream portion of the channel, the first capture array including a plurality of first forward funnels along a direction orthogonal to a flow direction of the sample so as to capture the different kinds of targets;
a second capture array arranged in a downstream portion of the channel, the second capture array including a plurality of second forward funnels arranged along the direction orthogonal to the flow direction of the sample so as to capture the different kinds of targets; and
a dispersing unit arranged between the inlet and the first capture array so as to disperse the flow of the sample,
wherein the dispersing unit includes a plurality of posts arranged in a spaced-apart relationship along the flow direction of the sample and along the direction orthogonal to the flow direction of the sample so that the different kinds of targets can pass through between the posts.

15. The micro-fluidic device of claim 14, wherein the posts includes odd-number post arrays and even-number post arrays arranged in a staggering pattern from an upstream portion of the channel toward a downstream portion of the channel.

16. The micro-fluidic device of claim 15, wherein the dispersing unit includes a plurality of dispersing units arranged in multiple stages along the flow direction of the sample, the posts arranged such that the diameter of the posts is gradually reduced along the flow direction of the sample.

17. A target separating method, comprising the steps of:
providing a micro-fluidic device including a filter case having a channel through which a sample containing different kinds of targets can flow and a plurality of capture arrays arranged in multiple stages along a flow direction of the sample, each of the capture arrays including a plurality of forward funnels arranged within the channel along a direction orthogonal to the flow direction of the sample so as to capture the different kinds of targets and a reverse flow guide means for causing the different kinds of targets captured in the forward funnels to flow in a direction opposite to the flow direction of the sample when the filter case is mounted in an overturned state;
supplying the sample into the channel to capture the different kinds of targets with the forward funnels;
turning the filter case upside down such that the forward funnels are arranged in an overturned state;
supplying a carrier fluid into the channel to discharge the different kinds of targets captured by the forward funnels out of the filter case; and
collecting the different kinds of targets discharged out of the filter case.

18. The target separating method of claim 17, further comprising the step of: dispersing the flow of the sample with a dispersing unit arranged at an upstream side of the capture arrays.

19. The target separating method of claim 18, wherein the channel is divided into a plurality of sub-channels connected to one another, the capture arrays arranged in the sub-channels, the reverse flow guide means including a plurality of reverse funnels alternately arranged with respect to the forward funnels.

* * * * *